US007220718B2

(12) United States Patent
Alpan et al.

(10) Patent No.: US 7,220,718 B2
(45) Date of Patent: May 22, 2007

(54) ORAL TREATMENT OF HEMOPHILIA

(75) Inventors: Oral Alpan, Rockville, MD (US); Tirumalai Kamala, Rockville, MD (US); Polly Matzinger, Bethesda, MD (US); William Hugold Velander, Blacksburg, VA (US)

(73) Assignees: United States of America as represented by the Secretary of the Department of Health and Human Services, Washington, DC (US); Virginia Tech Intellectual Properties, Inc., Blacksburg, VA (US)

( * ) Notice: Subject to any disclaimer, the term of this patent is extended or adjusted under 35 U.S.C. 154(b) by 72 days.

(21) Appl. No.: 10/485,696

(22) PCT Filed: Aug. 2, 2002

(86) PCT No.: PCT/US02/24544
§ 371 (c)(1),
(2), (4) Date: Feb. 2, 2004

(87) PCT Pub. No.: WO03/013244
PCT Pub. Date: Feb. 20, 2003

(65) Prior Publication Data
US 2004/0209829 A1 Oct. 21, 2004

Related U.S. Application Data

(60) Provisional application No. 60/310,150, filed on Aug. 3, 2001.

(51) Int. Cl.
*A61K 38/00* (2006.01)
*C12P 21/00* (2006.01)
*A01K 67/00* (2006.01)
*A01K 67/027* (2006.01)
*C12P 21/06* (2006.01)
*C12N 5/00* (2006.01)
*C12N 15/00* (2006.01)

(52) U.S. Cl. .................. 514/2; 435/69.1; 435/320.1; 435/325; 435/455; 800/4; 800/7; 800/8; 800/14; 800/17

(58) Field of Classification Search ............... 435/69.1, 435/325, 455; 800/7, 8; 514/2, 44
See application file for complete search history.

(56) References Cited

U.S. PATENT DOCUMENTS

| 4,348,384 | A | 9/1982 | Horikoshi et al. |
| 4,873,316 | A | 10/1989 | Meade et al. |
| 5,589,604 | A | 12/1996 | Drohan et al. |
| 5,880,327 | A | 3/1999 | Lubdon et al. |
| 5,948,407 | A | 9/1999 | McGuinness et al. |
| 6,046,380 | A | 4/2000 | Clark |
| 6,221,349 | B1 | 4/2001 | Couto et al. |
| 6,255,554 | B1 | 7/2001 | Lubon et al. |
| 6,344,596 | B1 | 2/2002 | Velander et al. |

FOREIGN PATENT DOCUMENTS

| EP | 0 294 910 A1 | 12/1988 |
| WO | WO 80/01456 | 7/1980 |
| WO | WO 95/27512 | 10/1995 |

OTHER PUBLICATIONS

Terada et al, Vox Sang. 80(1):61-62, 2001.*
Pasi et al, Lancet. 361(9371):1801-9, 2003.*
Clark et al,. "The Molecular Manipulation of Milk Composition," *Genome* 31:950-955 (1989).
Hemker et al., "Oral Treatment of Hæmophilia A by Gastrointestinal Absorption of Factor VIII Entrapped in Liposomes," *The Lancet*, pp. 70-71, Jan. 12, 1980.
Hennighausen, "Transgenic Factor VIII: The Milky Way and Beyond," *Nature Biotechnol.* 15:945-946 (1997).
High, "Gene-Based Approaches to the Treatment of Hemophilia," *Ann. N.Y. Acad. Sci.* 961:63-64 (2002).
Kaplan et al., "Factor VIII Inhibitors. Potential for Prevention of Inhibitor Formation by Immune Tolerance," *Semin Thromb Hemost.* 26:173-178 (2000).
Kay et al., "Gene Therapy for the Hemophilias," *Proc. Natl. Acad. Sci. USA* 96:9973-9975 (1999).
Lindgren et al., "Does Peroral Administration of Factor VIII Induce Oral Tolerance in Patients with Acquired Haemophilia A?," *Throm Haemost* 83:632-633 (2000).
Mariani et al., "Immune Tolerance to Factor VIII: The International Registry Data," *Adv. Exp. Med. Biol.* 386:201-208 (1995).
Morcöl et al., "The Porcine Mammary Gland as a Bioreactor for Complex Proteins," *Ann. N.Y. Acad. Sci.* 2:218-233 (1994).
Niemann et al., "Expression of Human Blood Clotting Factor VIII in the Mammary Gland of Transgenic Sheep," *Transgenic Res.* 8:237-247 (1999).
Paleyanda et al. "Transgenic Pigs Produce Functional Human Factor VIII in Milk," *Nature Biotechnol.* 15:971-975 (1997).
Roberts, "Induction of Immune Tolerance to Factor VIII: A Plea for Caution," *JAMA* 259:84-85 (1988).
Udall et al., "Development of Gastrointestinal Mucosal Barrier. I. The Effect of Age on Intestinal Permeability to Macromolecules," *Pediatr. Res.* 15:241-244 (1981).

(Continued)

*Primary Examiner*—Sumesh Kaushal
(74) *Attorney, Agent, or Firm*—Klarquist Sparkman, LLP

(57) ABSTRACT

Disclosed herein is a simple method for the treatment of antigen-deficiency diseases, by orally administering to a subject a therapeutically effective amount of the deficient antigen, wherein the antigen is not present in a liposome. In one embodiment, the method increases hemostasis in a subject having hemophilia A or B, by orally administering to the hemophiliac a therapeutically effective amount of the appropriate clotting factor other than in a liposome, sufficient to induce oral tolerance and supply exogenous clotting factor to the subject.

28 Claims, 7 Drawing Sheets

OTHER PUBLICATIONS

Velander et al., "Transgenic Livestock as Drug Factories," *Sci Am.* 276:70-74 (1997).

Warshaw et al., "Intestinal Absorption of Intake Antigenic Protein," *Surgery* 76:495-499 (1974).

Wilmut et al., "Modification of Milk Composition," *J. Reprod. Fert. Suppl.* 41:135-146 (1990).

Yee et al., "Oral Immune Tolerance Induction to Factor VIII Via Breast Milk, a Possibility?," *Haemophilia* 6:591 (2000).

* cited by examiner

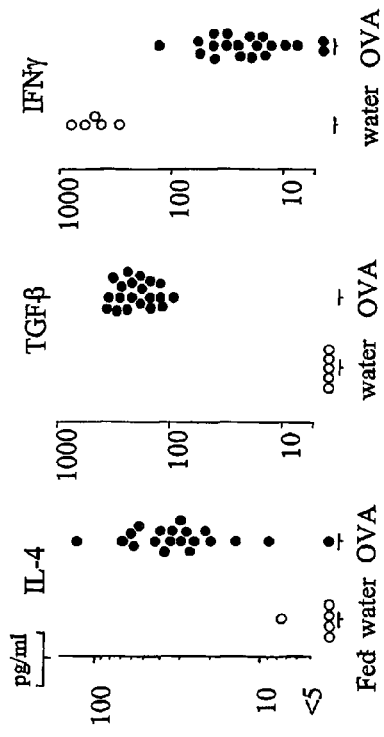
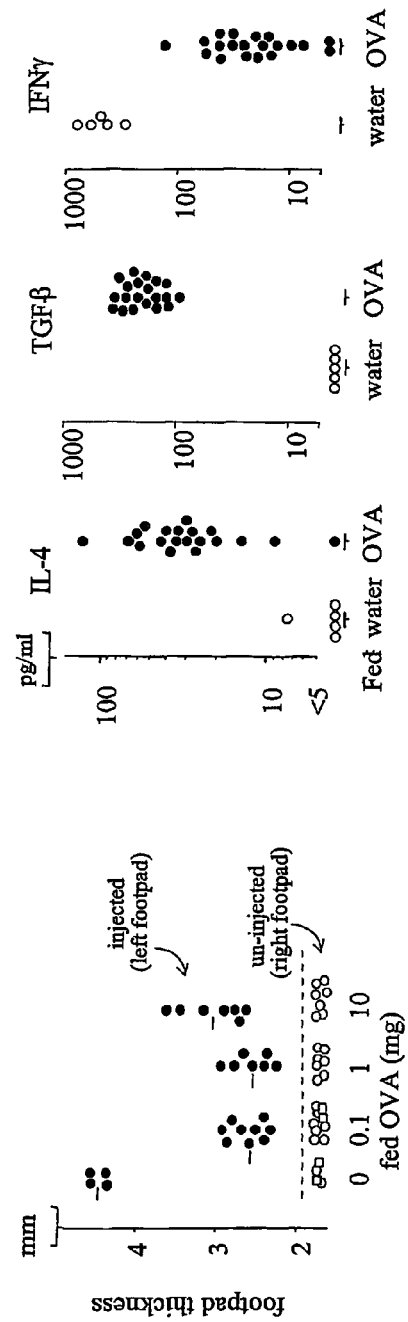
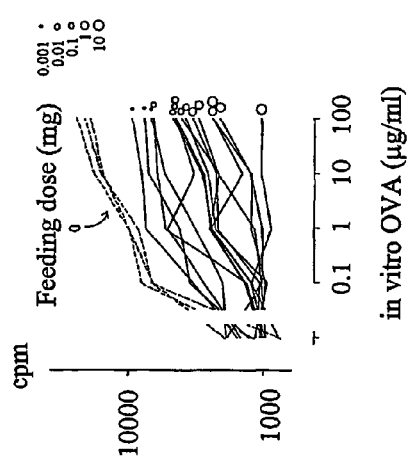

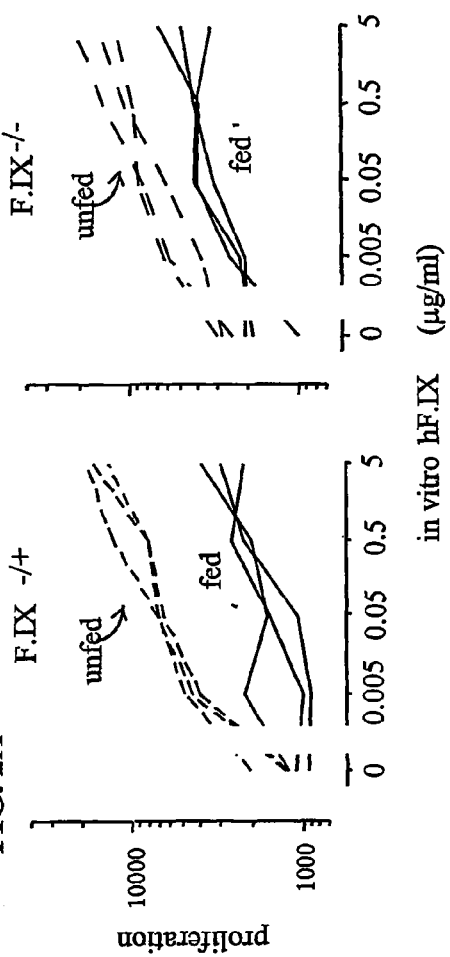
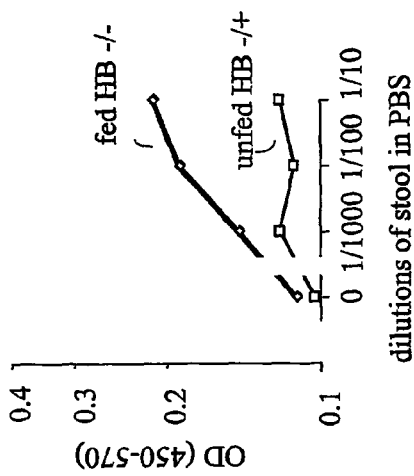
FIG. 2A  FIG. 2B  FIG. 2C

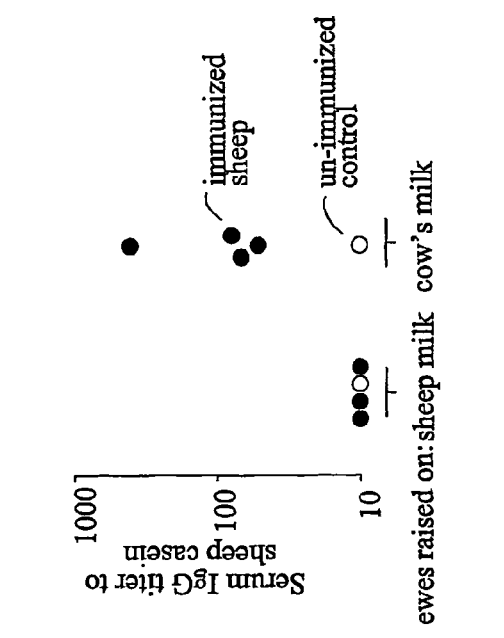
FIG. 5C
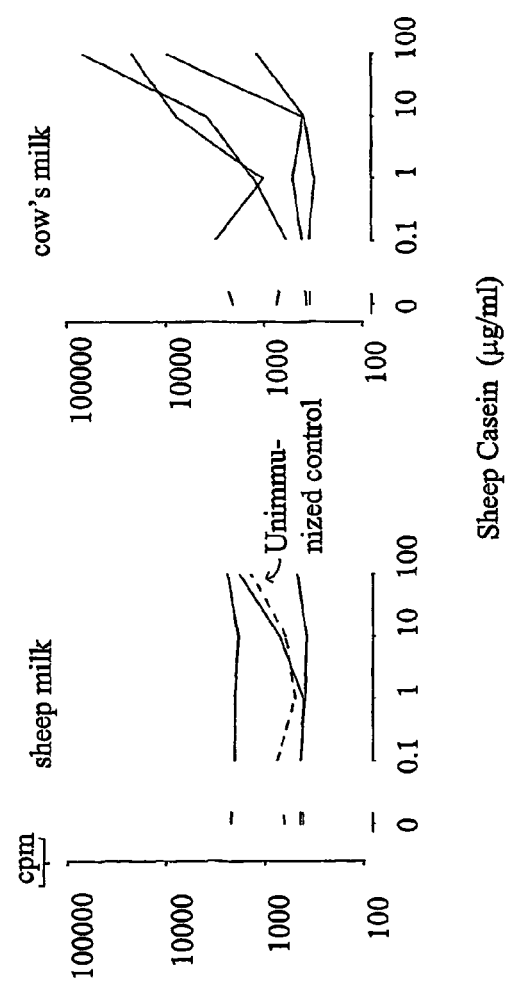
FIG. 5A
FIG. 5B

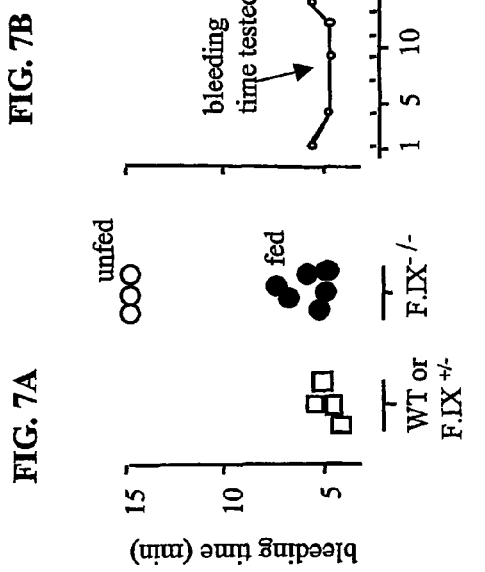
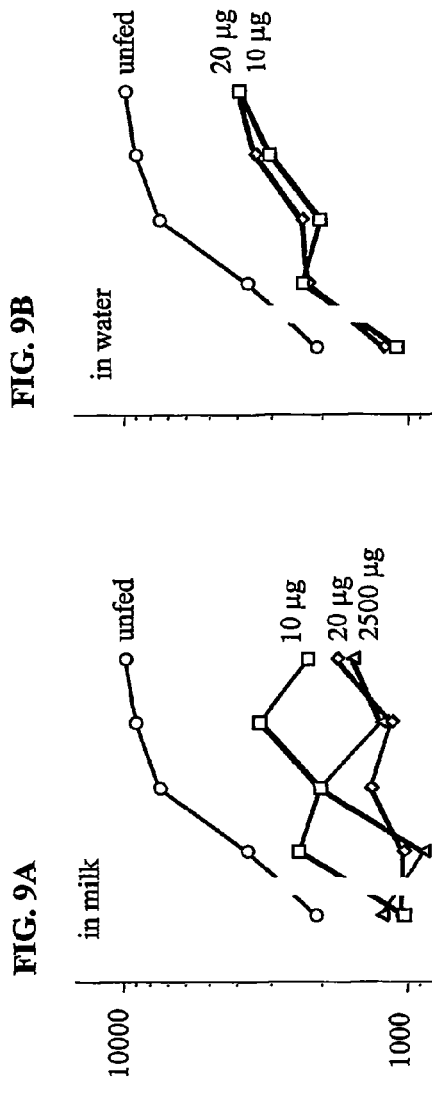

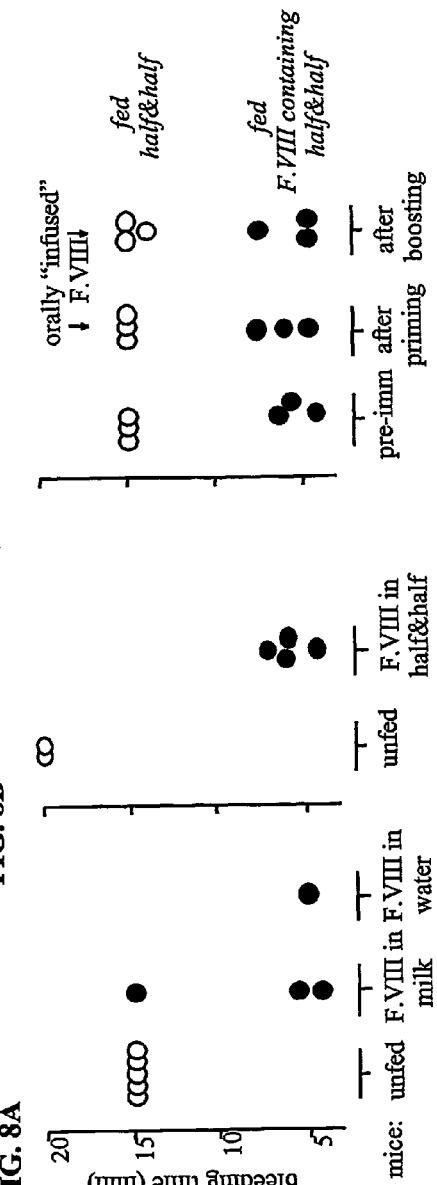
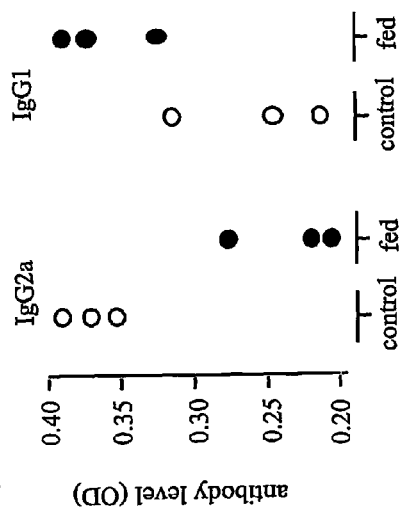
FIG. 8A  FIG. 8B  FIG. 8C  FIG. 8D

ORAL TREATMENT OF HEMOPHILIA

CROSS REFERENCE TO RELATED APPLICATION

This is a national stage under 35 U.S.C. §371 of International Application No. PCT/US02/24544, filed Aug. 2, 2002, and claims the benefit of U.S. Provisional application No. 60/310,150, filed Aug. 3, 2001, which is hereby incorporated by reference in its entirety.

FIELD

This disclosure relates to methods for treating a subject suffering from an antigen-deficiency which causes a disease, by orally administering a therapeutically effective amount of the deficient antigen to the subject, sufficient to induce oral tolerance and relieve symptoms of the disease. In one example, the disclosure relates to oral administration of clotting factor VIII or IX for treating hemophilia A and B, respectively.

BACKGROUND

Hemophilia A and B, caused respectively by decreased levels of clotting factor VIII (F.VIII) and IX (F.IX) levels in peripheral blood, are the most common severe inherited bleeding disorders. Although purified clotting factors from human plasma can be infused into these patients to prevent or treat bleeding episodes, this poses the risk of spreading of diseases such as Creutzfled-Jakob disease, HIV, and hepatitis C. Although recombinant clotting factor preparations are available, the supply is insufficient to cover the worldwide demand.

As an alternative to generating recombinant clotting factors in cell culture, the use of transgenic animals as bioreactors for the production of clinically useful quantities of proteins has been proposed. The transgenic animal expresses the desired protein in a body fluid, such as milk, from which the protein can readily be isolated. Transgenic pigs that secrete F.VIII (U.S. Pat. No. 5,880,327 to Lubon et al.) or F.IX (Van Cott et al. 1999. *Genet. Anal.* 15:155-60) in milk were generated using gene constructs that have regulatory sequences from the gene for mouse whey acidic protein (the 4.2 kb 5' promoter of WAP), in combination with the cDNA sequence encoding human F.VIII or F.IX. F.VIII pigs secrete 2.7 µg/ml of human F.VIII into milk (Paleyanda et al. 1997. *Nat. Biotech.* 15:971), while F.IX pigs secrete 2.5 g/L of human F.IX into milk, and the factor is biologically active as measured by an activated partial thromboplastin time assay (APTT).

Therefore, large amounts of functional protein can be obtained from F.IX pigs, which is purified from the milk, and subsequently administered intravenously (i.v.) to a hemophiliac patient. However, it has previously been thought that oral administration of F.VIII or F.IX results in degradation and/or inactivation of the protein due to the acidic and enzymatic composition of the stomach. For example, U.S. Pat. No. 4,348,384 to Horikoshi et al. teaches the administration of an oral composition containing purified F.VIII or F.IX encapsulated in a liposome along with a protease inhibitor, for the purpose of evading gastric inactivation of the therapeutic protein.

One complication that results from i.v. administration of F.VIII or F.IX is that up to 25% of hemophiliacs develop inhibitors, such as antibodies against F.VIII or F.IX that inactivate their procoagulant activity (Fields et al. 2000. *Mol. Ther.* 3:225-35; Bristol et al. 2001. *Hum. Gene Ther.* 12:1651-61; Ge et al. 2001. *Blood* 97:3733-7; Brinkhous et al. 1996. *Blood* 88:2603-10). Most inhibitory antibodies develop in severely affected patients who have little or no circulating F.IX or F.VIII antigen due to genetic deletion. However, patients with a family history of inhibitor development, severe disease, older age or higher numbers of clotting factor replacement episodes, also have a higher incidence of developing these inhibitors (Roberts. 1997. Inhibitors and their management. In *Hemophilia & other inherited bleeding disorders*. Rizza & Lowe, eds. W B Saunders Company Ltd., London, p. 365.). The inhibitors can completely inhibit the activity of infused clotting factor and make further treatment difficult.

One means of reducing clotting factor antibodies is the induction of immune tolerance to the clotting factors. For example, Roberts (*JAMA* 259:84-5, 1988) reviews studies in which F.VIII was injected at high concentrations. Although some studies reported that the level of anti-factor VIII antibodies decreased, due to the high doses required, the method was never widely used because it was prohibitively expensive. Oral administration of F.VIII as a means to prevent the formation of anti-F.VIII antibodies has also been attempted, with mixed results. Oral administration of purified F.VIII to newborn mice did not suppress induction of anti-F.VIII antibodies (Kaplan et al. 2000. *Semin. Thromb. Hemost.* 26:173-8). Oral administration of purified F.VIII to one of three patients with acquired hemophilia did reduce the amount of anti-F.VIII antibodies (Lindgren et al. 2000. *Thromb. Haemost.* 83:632-3). However, there are no teachings that oral administration of clotting factors alone can be used to treat hemophilia which is caused by inadequate expression of a clotting factor.

Attempts to induce stable production of the missing clotting factors by gene therapy using injections of transfected myoblasts have also been hampered by the host immune system which, not being tolerant of the missing factor, generates a strong rejection response when introduced (Fields et al. 2000. *Mol. Ther.* 3:225-35). Thus, inhibitory antibodies to the factors and vigorous T cell responses to the genetically transfected cells are major hurdles to successful treatment of hemophilia.

Another disadvantage to introduction of a foreign gene through the use of a viral vector, is the possibility of an elicited immune response against the vector and/or the transgene product For example, intramuscular (i.m.) injection of an adenoviral vector expressing human F.IX into the hind limbs of hemophiliac mice results in a CTL response against F.IX, and destruction of the transduced cells, whereas i.m. injection of a less immunogenic vector (adeno-associated virus, AAV) expressing human F.IX results in long-term persistence of the transduced cells and an absence of CTL to F.IX (Roberts. 1997. Inhibitors and their management. In *Hemophilia & other inherited bleeding disorders*. Rizza & Lowe, eds., W B Saunders Company Ltd., London, p. 365.). However, in both cases formation of antibodies neutralizes F.IX activity. The same problem exists in the canine model of hemophilia B, where anti-F.IX antibodies neutralize F.IX activity after gene therapy with F.IX (Evans et al. 1989. *Proc. Natl. Acad. Sci. U S A*. 86:10095-9; Mauser et al. 1996. *Blood*. 88:3451-5; Herzog et al. 1999. Nat. Med. 5:56-63; and Kay et al. 2000. *Nat. Genet.* 24:257-261).

SUMMARY OF THE DISCLOSURE

Although potentially large amounts of functional protein can be obtained from F.IX pigs, the current teaching has been to purify the factor from the milk, and subsequently administer it intravenously (i.v.) to a hemophiliac patient. However, it would be advantageous if the protein could be delivered orally, as oral administration is more easily handled than injection, and may eliminate the need for protein purification. In addition, it would be beneficial if oral tolerance to clotting factors could be induced by oral administration of the clotting factor.

Disclosed herein is a method for treating an antigen-deficiency disease by orally administering a therapeutically effective amount of the deficient antigen. In one non-limiting example, the method is a method for increasing hemostasis in a subject having a hemophilia caused by inadequate expression of a clotting factor, by orally administering a therapeutically effective amount of a clotting factor other than in a liposome. In another example, the method is a method for decreasing the symptoms associated with Gaucher disease (such as decreasing hepatosplenomegaly and improving bone marrow involvement), in a subject having Gaucher disease caused by decreased expression of acid beta-glucosidase, by orally administering a therapeutically effective amount of a acid beta-glucosidase.

BRIEF DESCRIPTION OF THE FIGURES

FIG. 1A is a dot-plot comparing the footpad swelling in mice fed OVA prior to injection (0.1-10 mg OVA) with control mice not fed OVA prior to injection (0 mg OVA).

FIG. 1B shows three dot-plots comparing the amount of IL-4, TGF-$\beta$, and IFN-$\gamma$ production in mice fed OVA prior to injection, with control mice not fed OVA (water) prior to injection.

FIG. 1C is a graph comparing the amount of T-cell proliferation in mice fed OVA prior to injection (0.001-10 mg OVA) with control mice not fed OVA prior to injection (0 mg OVA).

FIGS. 2A and 2B are graphs comparing the amount of T-cell proliferation in (A) normal and (B) hemophilia B mice fed human F.IX prior to injection, with control mice not fed human F.IX prior to injection.

FIG. 2C is a graph comparing the level of IgA produced in F.IX-fed hemophilia B mice to unfed normal mice.

FIGS. 5A and 5B are graphs comparing the proliferative response against sheep casein, in lambs fed (A) sheep milk or (B) cow milk.

FIG. 5C is a dot plot comparing the serum IgG titer to sheep casein in lambs raised on sheep milk compared to cow milk.

FIG. 7A is a dot plot showing that orally administered F.IX remains functional, and corrects the bleeding defect in hemophilia B mice.

FIG. 7B is a graph showing that orally administered F.IX remains functional, and corrects the bleeding defect in hemophilia B mice fed F.IX milk for 2 months.

FIGS. 8A and 8B are dot plots showing that orally administered F.VIII remains functional, whether administered in water or in cow's milk.

FIG. 8C is a dot plot showing that immunization following oral administration of F.VIII does not inhibit F.VIII fed subsequent to the immunization.

FIG. 8D is a dot plot showing IgG1 and IgG2a antibody responses to hF.VIII.

FIGS. 9A and 9B are graphs comparing the T cell response in mice fed F.IX in water or milk showing that oral administration of F.IX can be achieved whether administered in water or in milk, but that it is more effective if given in milk.

DETAILED DESCRIPTION OF SEVERAL EMBODIMENTS

Abbreviations and Terms

Figures 3A, 3B, 4:
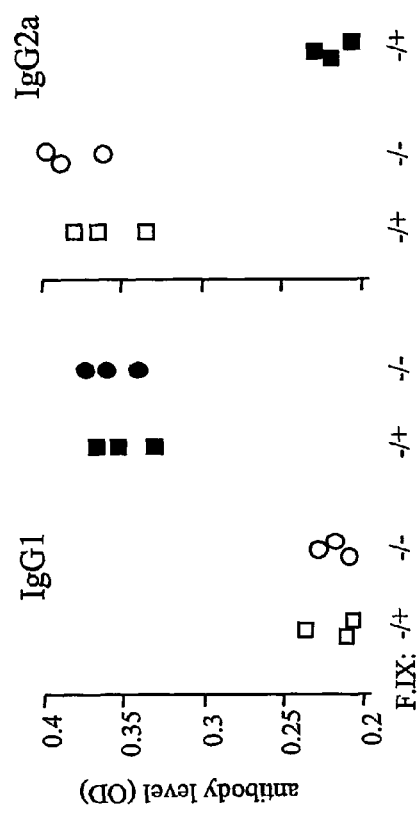
FIGS. 3A and 3B are dot plots showing (A) IgG1 and (B) IgG2a antibody responses to hF.IX.
FIG. 4 is a dot plot showing that orally tolerized hemophilia B mice show little evidence of inhibitors, as their bleeding times are only slightly longer than those of infused mice that had not been immunized.

The following explanations of terms and methods are provided to better describe the present disclosure and to guide those of ordinary skill in the art in the practice of the present disclosure. As used herein and in the appended claims, the singular forms "a" or "an" or "the" include plural references unless the context clearly dictates otherwise. For example, reference to "a protein" includes a plurality of such proteins and reference to "the antibody" includes reference to one or more antibodies and equivalents thereof known to those skilled in the art, and so forth.

Unless explained otherwise, all technical and scientific terms used herein have the same meaning as commonly understood to one of ordinary skill in the art to which this disclosure belongs.

Antigen: A substance capable of being the target of inducing a specific immune response.

Antigen-Deficiency Disease: A disease in which a subject has an antigen deficiency, such as a protein, which causes the disease. Examples of antigen-deficiency diseases include, but are not limited to clotting disorders such as hemophilia A and B (caused by a deficiency of clotting factor VIII and IX, respectively), Von Willebrand's disease (caused by a moderate-to-severe factor VIII deficiency, low-levels of factor VIII-related antigen, and insufficient von Willebrand factor); and diabetes (caused by a deficiency of insulin).

Other examples of antigen deficiency diseases include, but are not limited to: strokes or heart attacks (deficiency of tissue plasminogen activator); emphysema (deficiency of alpha-1-antitrypsin); Gaucher disease (deficiency of $\beta$-glucosidase), Pompe's disease (deficiency of alpha-1,4-glucosidase); purpura fulminans neonatalis, warfin-induced skin necrosis, heparin-induced thrombocytopenia, septic shock, and for fibrinolytic therapy (deficiency of protein C) (also see U.S. Pat. No. 5,589,604).

In a particular embodiment, the treatment of such diseases can be achieved by orally administering the deficient antigen to a subject having the disease.

Anti-immune therapy: Administration of agents to a subject having an autoimmune disease to reduce the immune response against normal body tissue while leaving intact the immune response against micro-organisms and abnormal tissues. Examples of agents used to reduce the immune response include, but are not limited to: corticosteroids and immunosuppressant medications (including prednisolone, cyclophosphamide or azathioprine) or cytotoxic agents such as cytoxan or methotrexate.

Activated partial thromboplastin time (APTT) Assay: An assay that measures the time it takes plasma to clot. APTT is the period required for clot formation in recalcified blood plasma after contact activation and the addition of platelet substitutes (e.g., brain cephalin or similar phospholipids). In normal individuals, the APTT is about 30-40 seconds, and the PTT (therapeutic level) is 60 to 70 seconds. A prolonged APTT can indicate a deficiency of a number of clotting factors including Factors XII, XI, IX, VIII, X, V, and II, and fibrinogen.

Bleeding Time Assay: An assay used to measure the amount of time it takes for a subject's blood to clot. A blood pressure cuff is placed on the upper arm and inflated. Two incisions are made on the lower arm. These are about 10 mm (less than ½ inch) long and 1 mm deep (just deep enough to cause minimal bleeding). The blood pressure cuff is immediately deflated. Blotting paper is touched to the cuts every 30 seconds until the bleeding stops. The length of time it takes for the cuts to stop bleeding is recorded.

In normal, non-hemophiliacs, bleeding stops within about one to ten minutes and may vary from lab to lab, depending on how the assay is measured. In contrast, severe hemophiliacs having less than 1% of normal levels of the appropriate clotting factor have a whole blood clotting time of greater than 60 minutes.

In mice, the bleeding time is assayed by transecting the tip of the tail and periodically touching a blotting paper until a clot is formed at the tip of the tail. Normal bleeding time is between 2-4 minutes. In contrast, hemophiliac mice having less than 1% of normal levels of the appropriate clotting factor have a bleeding time of greater than 15 minutes (see FIGS. 7A, 7B, 8A and 8B).

cDNA (complementary DNA): A piece of DNA lacking internal, non-coding segments (introns) and regulatory sequences which determine transcription. cDNA can be synthesized in the laboratory by reverse transcription from messenger RNA extracted from cells.

Chemical synthesis: An artificial means by which one can make a protein or peptide. A synthetic protein or peptide is one made by such artificial means.

Clotting disorder: A disease resulting in a defect in hemostasis in a subject. In one embodiment, it is a disease of the blood clotting (coagulation) system in which bleeding is prolonged due to inadequate clotting factors in the blood, for example inadequate expression of the clotting factor, such as inadequate expression due to a genetic abnormality. Normal blood hemostasis is a complex process involving as many as 20 different plasma proteins, known as clotting factors. Normally, a complex chemical process occurs using these clotting factors to form a substance called fibrin that stops bleeding. When certain coagulation factors are deficient or missing, the process does not occur normally. Bleeding problems can range from mild to severe.

Some bleeding disorders are present at birth and in some instances are inherited disorders. Specific examples include, but are not limited to: hemophilia A, hemophilia B, protein C deficiency, and Von Willebrand's disease. Some bleeding disorders are developed during certain illnesses (such as vitamin K deficiency, severe liver disease), or treatments (such as use of anticoagulant drugs or prolonged use of antibiotics).

Clotting factor: Includes any protein which promotes proper hemostasis. In one embodiment, a clotting factor is factor VIII (F.VIII) or factor IX (F.IX), or a variant or fragment thereof which retains its hemostatic activity, for example as measured using an APTT assay or a bleeding time assay. In another embodiment, when orally administered in a therapeutically effective amount, the clotting factor increases hemostasis in a subject suffering from a clotting disorder, such as hemophilia. In a particular embodiment, a clotting factor is a recombinant clotting factor, wherein expression of a DNA encoding the clotting factor in a mammal results in the presence of the recombinant clotting factor protein in the milk of the transgenic mammal.

Comprises: A term that means "including." For example, "comprising A or B" means including A or B, or both A and B, unless clearly indicated otherwise.

Deletion: The removal of a sequence of a nucleic acid, for example DNA, the regions on either side being joined together.

DNA: Deoxyribonucleic acid. DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Enhance: To improve the quality, amount, or strength of something. In one embodiment, a therapy enhances or increases hemostasis in a subject (such as a hemophiliac) if the subject is more effective at blood clotting (for example, their blood clotting time decreases). Such enhancement can be measured using the methods disclosed herein, for example determining the bleeding time of a subject using an APTT or bleeding time assay.

Factor VIII (F.VIII) F.VIII is a protein required for the efficient clotting of blood, and functions in coagulation as a cofactor in the activation of factor X by factor IX. A concentration of about 100 ng/ml for F.VIII in the blood is considered in the normal range. Deficiency of F.VIII is associated with hemophilia A, and severe forms of the disease can result when a subject has less than about 1% of the normal amount of F.VIII (i.e. less than about 1 ng of F.VIII per ml of blood). F.VIII is synthesized as a 2351 amino acid single chain precursor protein, which is proteolytically processed. The human factor VIII gene (186,000 base-pairs) consists of 26 exons ranging in size from 69 to 3,106 bp and introns as large as 32.4 kilobases (kb). Examples of F.VIII nucleic acid and protein sequences, including variants and fragments thereof, and sequences from different organisms, are publicly available on Genbank (for example see Accession Nos: K01740, M14113, and E00527 (human); AF016234 (canine); and L05573 (mouse)).

Gaucher Disease: An autosomal-recessive disorder that results from defective activity of acid β-glucosidase. Disease variants are classified based on the absence or presence and severity of neuronopathic involvement. Enzyme therapy is currently the treatment of choice in significantly affected patients. For example, cerezyme, a recombinantly produced mannose-terminated (macrophage-targeted) acid β-glucosidase, is currently used to diminish hepatosplenomegaly and improve bone marrow involvement and hematologic findings. However, it is possible that oral administration of β-glucosidase using the methods disclosed herein, can be used to alleviate one or more symptoms associated with Gaucher disease described below.

Type 2 Gaucher disease is a rare, severe CNS disease that leads to death by 2 years of age.

Type 3 Gaucher disease has highly variable manifestations in the CNS and viscera. It can present in early childhood with rapidly progressive, massive visceral disease and slowly progressive to static CNS involvement; in adolescence with dementia; or in early adulthood with rapidly progressive, uncontrollable myoclonic seizures and mild visceral disease. Visceral disease in type 3 is nearly identical to that in type 1, but is generally more severe. Early CNS findings may be limited to defects in lateral gaze tracking, which may remain static for decades. Mental retardation can be slowly progressive or static.

Type 1 Gaucher disease is a highly variable nonneuronopathic disease. Younger patients tend to have a greater degree of hepatosplenomegaly and accompanying blood cytopenias. Older patients have a greater tendency for chronic bone disease. Hepatosplenomegaly occurs in virtually all symptomatic patients and can be minor or massive. Accompanying anemia and thrombocytopenia are variable and not linearly related to liver or spleen volume. Severe liver dysfunction is unusual, though minor liver function abnormalities are common. Splenic infarctions can resemble an acute abdomen. Pulmonary hypertension and alveolar Gaucher cell accumulation are uncommon, but life-threatening.

Though it is more common in adult patients, clinically evident skeletal disease in children can be devastating, resulting in massive destruction of the axial and peripheral skeleton. All patients with Gaucher disease have non-uniform infiltration of bone marrow by lipid-laden macrophages, termed Gaucher cells. This can lead to marrow packing with subsequent infarction, ischemia, necrosis, and cortical bone destruction. Bone marrow involvement spreads from proximal to distal in the limbs and can involve the axial skeleton extensively, causing vertebral collapse. In addition to bone marrow involvement, bone remodeling is defective, with loss of total bone calcium leading to osteopenia, osteonecrosis, avascular infarction, and vertebral compression fractures and spinal cord involvement. Aseptic necrosis of the femoral head is common, as is fracture of the femoral neck.

Affected patients experience chronic, ill-defined bone pain that can be debilitating. Some patients have one or more "bone crises" in their lifetimes that are associated with localized, excruciating pain, and, on occasion, local erythema, fever, and leukocytosis. Any bone can be involved, though the femurs and vertebral bodies are affected most often. These crises represent acute infarctions of bone, as evidenced in nuclear scans by localized absent uptake of pyrophosphate agents. X-rays are usually negative initially but may show lytic lesions 4 to 6 months after the acute phase.

The diagnosis of Gaucher disease is established by demonstrating decreased acid β-glucosidase activity (0 to 20% of normal) in nucleated cells. The enzyme is not present in bodily fluids. The sensitivity of enzyme testing is poor for detecting heterozygous carriers; molecular testing is preferred when the mutations are known. Four common mutations account for ~90 to 95% of the mutations in affected patients: N370S (1226G), 84GG (a G insertion at cDNA position 84), L444P (1448C), and IVS-2 (an intron 2 splice junction mutation). Genotype/phenotype studies indicate a significant correlation, though not absolute, between disease type and severity and the acid β-glucosidase genotype.

Factor IX (F.IX): F.IX is a vitamin K-dependent protein required for the efficient clotting of blood, and functions in coagulation as an activator of factor X. A concentration of about 1-5 μg/ml of F.IX in the blood is considered in the normal range. Deficiency of F.IX is associated with hemophilia B, and severe cases result when the concentration of F.IX is less than about 1% of the normal concentration of F.IX (i.e. less than about 0.01-0.05 μg F.IX per ml of blood). Canine F.IX possesses 86% identity at the amino-acid level with human F.IX (Evans et al. 1989. *Blood* 74:207-12). F.IX nucleic acid and protein sequences, including variants and fragments thereof, and sequences from different organisms, are publicly available (for example see Kurachi et al., 1982. *Proc. Nat. Acad. Sci. U.S.A.* 79(21):6461-4; Genbank Accession Nos: J00136, XM_045316, K02402, J00137, and M11309 (human) and M21757 and M33826 (canine)).

Hemophilia: A blood coagulation disorder caused by a deficient clotting factor activity, which decreases hemostasis. Severe forms result when the concentration of clotting factor is less than about 1% of the normal concentration of the clotting factor in a normal subject. In some subjects, hemophilia is due to a genetic mutation which results in impaired expression of a clotting factor. In others, hemophilia is an auto-immune disorder, referred to as acquired hemophilia, in which the antibodies which are generated against a clotting factor in a subject result in decreased hemostasis.

Hemophilia A results from a deficiency of functional clotting factor VIII (F.VIII), while hemophilia B results from a deficiency of functional clotting factor IX (F.IX). These conditions which are due to a genetic mutation are caused by an inherited sex-linked recessive trait with the defective gene located on the X chromosome, and this disease is therefore generally found only in males. The severity of symptoms can vary with this disease, and the severe forms become apparent early on. Bleeding is the hallmark of the disease and typically occurs when a male infant is circumcised. Additional bleeding manifestations make their appearance when the infant becomes mobile. Mild cases may go unnoticed until later in life when they occur in response to surgery or trauma. Internal bleeding may happen anywhere, and bleeding into joints is common.

Hemophiliac: A subject having a hemophilia.

Hemostasis: Arrest of bleeding blood by blood clot formation. When hemostasis is increased, it is increased relative to hemostasis in a subject prior to orally administering a therapeutically effective amount of the appropriate clotting factor to the subject. In one embodiment, when hemostasis increases in a subject with hemophilia, the blood clotting time decreases. Blood clotting time is the length of time it takes for peripheral blood to clot using an activated partial thromboplastin time assay (APTT, see EXAMPLE 9) or by measuring bleeding time (see above and EXAMPLE 5). In a particular embodiment, the blood clotting time decreases by at least 50%, for example at least 60%, at least 70%, at least 75%, at least 80%, at least 90%, at least 95%, at least 98%, at least 99% or even about 100% (i.e. the blood clotting time is similar to what is observed for a normal subject) when compared to the blood clotting time of the subject prior to orally administering to the subject a therapeutically effective amount of the appropriate clotting factor. In yet another embodiment, the blood clotting time in the affected subject is corrected to about 90% of a normal subject, for example to about 95%, for example about 100%, after oral administration of a therapeutically effective amount of the appropriate clotting factor.

Impaired Expression: Decreased expression of a DNA or protein resulting in a deficiency of the protein in a subject. Such a protein deficiency may cause disease in the subject.

Isolated: An isolated nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

Liposome: A closed, solvent-filled vesicle bounded by a single bilayer of phospholipids, which is impermeable to many substances. In one embodiment, a liposome has the properties described in U.S. Pat. No. 4,348,384 to Horikoshi et al. (herein incorporated by reference).

Mammal: This term includes both human and non-human mammals. Similarly, the terms "patient," "subject," and "individual" includes both human and veterinary subjects. Examples of mammals include, but are not limited to: humans, pigs, cows, goats, cats, dogs, rabbits and mice.

Normal Cells: Non-disease cells. In one embodiment, normal cells are cells obtained from a healthy subject, for example as compared to a hemophilic or diabetic subject.

Normal Subject: A subject who does not have an antigen-deficiency disease. For example, a subject who does not have hemophilia A or B.

Oligonucleotide: A linear polynucleotide sequence of up to about 200 nucleotide bases in length, for example a polynucleotide (such as DNA or RNA) which is at least about 6 nucleotides, for example at least 15, 50, 100 or 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Oral administration: A method of delivering an agent to a subject by mouth. In one embodiment, oral administration is achieved by feeding the agent to the subject. In a particular embodiment, the agent is an antigen, such as a protein, for example F.VIII or F.IX. The agent can be delivered with one or more pharmaceutically acceptable carriers which are not liposomes. In addition, the agent and one or more therapeutically effective pharmaceutical compounds can be administered concurrently or separately.

Oral tolerance: A method of downregulating an immune response in a subject by orally administering an antigen (i.e. by feeding) to the subject. Oral tolerance is characterized by decreased levels of systemic antibody production, as well as decreased delayed type hypersensitivity responses (DTH), T cell proliferation, cytotoxic responses and graft rejection (Alpan et al. 2001. *J. Immunol.* 166:4843-52; Chen et al. 1995. *Nature* 376:177-80; Weiner. 1997. *Imm. Today.* 7:335-44; Sayegh et al. 1992. *Transplantation.* 53:163-6).

The tolerogenic effect due to administration of high doses oral antigen is deletion of antigen-specific T cells by apoptosis (Weiner. 1997. *Imm. Today.* 7:335-44). Administration of low doses of oral antigen induces a switch in effector class such that Th1 type responses (DTH, cytotoxicity, graft rejection and complement fixing antibodies) are supplanted by Th3 type responses (the production of IL-4, IL10, TGF-β and, occasionally, secretory IgA) (Weiner. 1997. *Imm. Today.* 7:335-44). Low dose oral tolerance reduces the severity of EAE (Fields et al. 2000. *Molecular Therapy.* 3:225-35) and enables the acceptance of foreign transplants.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Purified: The term purified does not require absolute purity; rather, it is intended as a relative term. Thus, for example, a purified clotting factor preparation is one in which the factor is more pure than the factor in its natural environment within a cell. For example, a preparation of a clotting factor protein is purified if the protein represents at least 50%, for example at least 70%, of the total protein content of the preparation. Methods for purification of proteins and nucleic acids are well known in the art. Examples of methods that can be used to purify an antigen, such as a clotting factor include, but are not limited to the methods disclosed in Sambrook et al. (*Molecular Cloning: A Laboratory Manual*, Cold Spring Harbor, N.Y., 1989, Ch. 17); U.S. Pat. No. 6,005,082 to Smeds; EP 0294910 to van Ooyen et al.;

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. A recombinant protein is one that results from expressing a recombinant nucleic acid encoding the protein.

RT: Room temperature

Sample: Biological samples containing genomic DNA, cDNA, RNA, or protein obtained from the cells of a subject, such as those present in peripheral blood, urine, saliva, tissue biopsy, surgical specimen, fine needle aspriates, amniocentesis samples and autopsy material.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids. Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, 75%, 80%, 85%, 90%, 95%, or even 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

Protein homologs are typically characterized by possession of at least 70%, such as at least 75%, 80%, 85%, 90%, 95% or even 98% sequence identity, counted over the full-length alignment with the amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG.

One of skill in the art will appreciate that these sequence identity ranges are provided for guidance only; it is possible that strongly significant homologs could be obtained that fall outside the ranges provided. Provided herein are the peptide homologs described above, as well as nucleic acid molecules that encode such homologs.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous peptides can, for example, possess at least 75%, 80%, 90%, 95%, 98%, or 99% sequence identity determined by this method. When less than the entire sequence is being compared for sequence identity, homologs can, for example, possess at least 75%, 85% 90%, 95%, 98% or 99% sequence identity over short windows of 10-20 amino acids. Methods for determining sequence identity over such short windows can be found at the NCBI web site. One of skill in the art will appreciate that these sequence identity ranges are provided for guidance only; it is possible that significant homologs or other variants can be obtained that fall outside the ranges provided.

Subject: Living multicellular vertebrate organisms, a category which includes, both human and veterinary subjects for example, mammals, rodents, and birds.

Therapeutically Effective Amount: An amount sufficient to achieve a desired biological effect, for example an amount that is effective to increase hemostasis. In particular examples, it is a concentration of clotting factor, such as F.VIII or F.IX, effective to increase hemostasis, such as in a subject to whom it is administered, such as a hemophiliac. In other examples, it is an amount effective to increase hemostasis by more than a desired amount.

In one embodiment, the therapeutically effective amount also includes a quantity of clotting factor (such as a clotting factor protein or nucleic acid) sufficient to achieve a desired effect in a subject being treated. For instance, these can be an amount necessary to improve signs and/or symptoms a disease such as hemophilia, for example by increasing hemostasis.

An effective amount of a clotting factor can be administered in a single dose, or in several doses, for example daily, during a course of treatment. However, the effective amount of clotting factor will be dependent on the source of clotting factor administered (i.e. clotting factor isolated from a blood sample versus recombinant clotting factor expressed in milk), the subject being treated, the severity and type of the condition being treated, and the manner of administration clotting factor. For example, a therapeutically effective amount of clotting factor can vary from about 0.01 mg/kg body weight to about 5 g/kg body weight, for example, at least 5 mg/kg daily, for example at least 50 mg/kg daily. In other embodiment, it is a concentration of F.VIII, when orally administered, which results in a blood concentration of greater than about 1 ng F.VIII per ml blood, for example greater than about 10 ng per ml, for example about 100 ng per ml. In yet another embodiment, it is a concentration of F.IX, when orally administered, which results in a blood concentration of greater than about 0.01-0.05 µg F.IX per ml blood, for example greater than about 0.1-0.5 µg per ml, for example about 1-5 µg per ml.

The methods disclosed herein have equal application in medical and veterinary settings. Therefore, the general term "subject being treated" is understood to include all animals (e.g. humans, apes, dogs, cats, horses, and cows) that require an increase in the desired biological effect, such as enhanced hemostasis susceptible to clotting factor-mediated modulation.

Therapeutically effective dose: A dose of antigen sufficient to increase the amount of that antigen in a subject to whom it is administered, resulting in a regression of a pathological condition, or which is capable of relieving signs or symptoms caused by the condition. In a particular embodiment, it is a dose of clotting factor sufficient to increase hemostasis in a hemophiliac.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgenic Cell: Transformed cells which contain foreign, non-native DNA.

Transgenic mammal: Transformed mammals which contain foreign, non-native DNA. In one embodiment, the non-native DNA is an antigen, such as human F.VIII or human F.IX. In a particular embodiment, a transgenic mammal expresses a recombinant clotting factor in its milk. In yet another embodiment, the transgenic animal is a pig expressing recombinant human F.VIII or F.IX in its milk. One skilled in the art will understand that any mammal can be used, including, but not limited to pigs, cows, goats, sheep, rats, mice, rabbits, dogs, cats, and primates.

Variants or fragments or fusion proteins: The production of protein which is orally administered can be accomplished in a variety of ways (for example see EXAMPLES 15 and 16). DNA sequences which encode for a protein or fusion protein, or a fragment or variant of a protein (for example a fragment or variant having 80%, 90% or 95% sequence identity to a blood clotting factor) can be engineered to allow the protein to be expressed in eukaryotic cells or organisms, bacteria, insects, and/or plants. To obtain expression, the DNA sequence can be altered and operably linked to other regulatory sequences. The final product, which contains the regulatory sequences and the therapeutic protein, is referred to as a vector. This vector can be introduced into eukaryotic, bacteria, insect, and/or plant cells. Once inside the cell the vector allows the protein to be produced.

A fusion antigen comprising a protein, such as F.VIII or F.IX (or variants, polymorphisms, mutants, or fragments thereof) linked to other amino acid sequences that do not inhibit the desired activity of the protein, for example the ability to increase hemostasis. In one embodiment, the other amino acid sequences are no more than 10, 20, 30, or 50 amino acid residues in length.

One of ordinary skill in the art will appreciate that the DNA can be altered in numerous ways without affecting the biological activity of the encoded protein. For example, PCR can be used to produce variations in the DNA sequence which encodes an antigen. Such variants can be variants optimized for codon preference in a host cell used to express the protein, or other sequence changes that facilitate expression.

Vector: A nucleic acid molecule as introduced into a host cell, thereby producing a transformed host cell. A vector can include nucleic acid sequences that permit it to replicate in the host cell, such as an origin of replication. A vector can also include one or more selectable marker genes and other genetic elements known in the art.

Additional definitions of terms commonly used in molecular genetics can be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Disclosed herein is a method for increasing hemostasis in a subject having a hemophilia by orally administering to the subject a therapeutically effective amount of a clotting factor not present in a liposome, sufficient to induce oral tolerance and supply exogenous clotting factor to the subject. In one embodiment, hemophilia is a result of impaired expression of a clotting factor. In yet another embodiment, increasing hemostasis comprises decreasing blood clotting time. For example, blood clotting time can be decreased by at least 50%, for example at least 60%, at least 70%, at least 80%, at least 85%, at least 90%, at least 95%, at least 98%, or even at least 99% compared to a blood clotting time of an untreated hemophilic subject. The blood clotting time can be measured using an activated partial thromboplastin time (APTT) assay or by a bleeding time assay.

In another embodiment, the clotting factor is administered in absence of an anti-immune therapy. In a particular embodiment, a therapeutically effective amount of a clotting factor is a daily dose of at least 5 mg of clotting factor per kg of subject, for example at least 50 mg of clotting factor per kg of subject. The clotting factor can be administered daily or every other day. The subject to be treated can be a mammal, for example a human or dog. The hemophilia can be hemophilia A and the clotting factor F.VIII, or hemophilia B and the clotting factor F.IX. In one embodiment, a therapeutically effective amount of F.VIII is at least 5 mg of clotting factor per 1 kg of subject daily and a therapeutically effective amount of F.IX is at least 50 mg of clotting factor per 1 kg of subject daily.

In a particular embodiment, oral administration is achieved by feeding the subject a therapeutically effective amount of the clotting factor. For example, the clotting factor can be a recombinant clotting factor present in milk of a transgenic mammal, which is fed to a hemophiliac. In one embodiment, the clotting factor, such as F.IX, is present in milk obtained from a transgenic pig expressing the clotting factor, such as recombinant F.IX. The clotting factors can be present in at least one pharmaceutically effective carrier, such as water or milk.

The methods disclosed herein can further include administering to a subject an isolated recombinant nucleic acid molecule encoding a clotting factor, such that the clotting factor is expressed in the subject.

Also disclosed herein is a method for increasing hemostasis in a subject having a hemophilia, which includes, and in some examples consists of, orally administering to the subject a therapeutically effective amount of a clotting factor and at least one pharmaceutically acceptable carrier which is not a liposome. In other examples, the pharmaceutical compositions disclosed herein (including clotting factors) can be administered in combination, or separately, with one or more other therapeutic treatments, such as other agents that increase hemostasis.

A method is also disclosed for orally administering a recombinant clotting factor to a subject for treatment of a hemophilia by orally administering milk containing recombinant clotting factor to the subject at a therapeutically effective amount such that hemostasis in the subject is increased, thereby treating the hemophilia. In one embodiment, the milk contains at least 2 g recombinant clotting factor/liter of milk. At this concentration, a 70 kg human would drink about 0.175 liters of milk daily to achieve an effective dose of about at least 5 mg/kg or about 1.75 liters of milk to achieve an effective dose of about at least 50 mg/kg. The milk can be obtained from a transgenic mammal, such as a pig which expresses the clotting factor (or other therapeutic protein) in its milk. In a particular example, the milk can contain recombinant F.IX antigen at a concentration of about 2 g per liter, for example about 2.5 g per L, either expressed in the milk or exogenously added to the milk.

Also disclosed herein is a method for orally administering a recombinant clotting factor to a subject for treatment of a hemophilia by expressing the clotting factor in a mammal such that the clotting factor is expressed in milk of the mammal and orally administering the milk in which the clotting factor has been expressed to the subject at a therapeutically effective amount such that blood clotting time in the subject is reduced, thereby treating the hemophilia. In a particular embodiment, the hemophilia is hemophilia B and the clotting factor is F.IX.

Further disclosed is a method for orally administering a recombinant F.IX protein to a subject for treatment of hemophilia B by orally administering milk containing recombinant F.IX protein at a therapeutically effective amount such that blood clotting time in the subject is reduced, thereby treating the hemophilia B.

Also disclosed is a method of orally administering to a hemophiliac a therapeutically effective amount of a clotting factor protein sufficient to induce oral tolerance to the clotting factor protein and supply exogenous clotting factor protein to the hemophiliac, wherein the clotting factor protein is not present in a liposome, and wherein oral tolerance prepares the hemophiliac for in vivo expression of a clotting factor gene. In a particular embodiment, the clotting factor is F.VIII or F.IX.

Disclosure of certain specific examples is not meant to exclude other embodiments.

EXAMPLE 1

Ovalbumin Oral Tolerance

This example describes the methods used to induce oral tolerance in mice to ovalbumin (OVA) by first orally administering OVA prior to immunization with OVA. Similar methods can be used to test any antigen of interest, such as F.VIII, F.IX, protein C, or insulin, in any animal/subject of interest.

Normal B10 mice were fed OVA by adding the protein to their drinking water for eight days at concentrations of 0.02, 0.2 or 2 mg/ml. The mice drank an average of 5.2 ml/mouse/ day. Therefore, the doses were 0.1, 1.0 and 10 mg/mouse/ day of OVA. Control mice only drank water. Two days after the last feeding, all mice were immunized with 50 µg OVA in complete Freund's adjuvant (CFA) (Sigma, St. Louis, Mo.) in the left footpad. Seven days later, footpad swelling was determined by measuring the thickness of the footpad. Measurement of the right (un-injected) footpad served as an untreated control. The footpad swelling responses were compared between injected, OVA-fed mice and injected, non-OVA fed control mice. As shown in FIG. 1A, the footpads of OVA-fed mice swelled less than those of the unfed group.

To compare the amount of IL4, TGF-β, and IFN-γ production, mice were fed 0.1 mg OVA for 10 days, then immunized as described above. Seven days after immunization, lymph nodes draining the immunization site were harvested and cultured in vitro with 100 µg/ml OVA. The culture was carried in 96 well round bottom plates, with 500,000 cells per well, for four days. For the last 8 hours of the culture, cells were pulsed with tritiated thymidine to assay for proliferation using a beta plate cell harvester. For IL-4 and IFN-γ, supernatants were assayed at day four. For TGF-β, after four days in culture, cells were washed, restimulated with APC and OVA in serum-free medium, and supernatants assayed at day three. ELISA assays were performed using commercially available kits from Endogen (Rockford, Ill.), according to the manufacturer's instructions. As shown in FIG. 1B, OVA-fed mice made high levels of IL-4 and TGF-β, but low levels of IFN-γ compared to mice in the unfed group.

To compare the amount of T-cell proliferation, mice were fed doses of OVA ranging from 0.001-10 mg every-other day for five feeds and immunized with 50 µg OVA in CFA. Seven days after immunization, lymph nodes draining the immunization site were harvested by surgical dissection. CD4 T-cells were purified from the lymph nodes and cultured in vitro with irradiated spleen cells and a graded concentration of OVA as described above. As shown in FIG. 1C, T cells in the draining lymph nodes of OVA-fed mice proliferated less than those mice in the unfed group. Since T cells in lymph nodes proliferate in response to regional antigenic stimulation, the reduction in T cell proliferation was a measure of decreased antigenic stimulation from OVA injection in the footpad.

EXAMPLE 2

Factor IX Oral Tolerance

This example describes experiments in which mice developed oral tolerance to F.IX by orally administering F.IX prior to immunization with F.IX, using the methods described in EXAMPLE 1.

Briefly, normal B10.A mice (F.IX−/+) or hemophilia B mice (F.IX−/−) were fed transgenic human F.IX (hF.IX) in pig milk (see EXAMPLE 5) or control pig milk (no hF.IX) every other day for three weeks. Individual mice drank about 4 ml (10 µg hF.IX/day/mouse) of the milk at each time. Two days after the last feeding, all mice were immunized with 50 µg human F.IX emulsified in CFA at the base of the tail. Eight days later, the amount of T cell proliferation was determined by culturing T-cells from the lymph nodes with graded concentrations of human F.IX (purified from the transgenic pig milk) for four days using the methods described in EXAMPLE 1. As shown in FIGS. 2A and 2B, feeding mice human F.IX had a similar effect to the result observed in EXAMPLE 1 for OVA, in that it decreased T cell proliferation upon subsequent immunization with human F.IX in CFA.

To demonstrate that oral administration of F.IX induces local immunity, hemophiliac B mice were fed transgenic F.IX in milk (see EXAMPLE 5) while normal mice did not receive F.IX, as described above. Subsequently the level of intestinal IgA to F.IX was measured by collecting stool samples, dissolving them in PBS, and assaying for IgA using standard ELISA methods. As shown in FIG. 2C, feeding F.IX induces local immunity as measured by the production of secretory IgA.

EXAMPLE 3

Antibodies Produced by Orally Tolerized Hemophilia B Mice Do Not Result in Clinical Resistance to Infused F.IX To measure IgG1 and IgG2a antibodies specific for hF.IX, plates were coated with hF.IX (10 µg/ml in PBS) then blocked with BSA overnight. After five washes, serum samples from the normal and hemophilia B mice fed as described in EXAMPLE 2 were added and incubated for two hours. The plates were then washed and subsequently incubated with HRP-conjugated goat-anti-mouse IgG1 and IgG2a for two hours, followed by TMP for color development, and plates subsequently read on an ELISA plate reader. As shown in FIGS. 3A and 3B, whereas unfed control mice made strong IgG2a antibodies, mice fed with hF.IX made no detectable IgG2a, but did produce IgG1.

Therefore, in normal mice, oral administration of human F.IX did not completely inhibit the production of small amounts of antibodies after immunization in CFA, as detected in ELISA assays, although it caused a shift from IgG2a to IgG1 (FIGS. 3A and 3B). However, CFA is the strongest adjuvant known, and may elicit antibody production that would not occur under conditions that more closely resemble a clinical situation. However, antibodies detectable in ELISA assays may bind to denatured proteins, but may not act as inhibitors of the native protein. Therefore, whether orally tolerized hemophiliac mice would made antibodies after CFA immunization, and whether these antibodies would act as inhibitors and lead to resistance to treatment, was determined.

Hemophilia B mice were fed transgenic F.IX milk, or fed milk without F.IX, every other day for two weeks. Two days after the last feeding, mice were immunized with h.FIX in CFA as described above. Nine days later, the tail vein was infused with a dose of F.IX just over the borderline for correcting the bleeding time (0.13 IU of functional hF.IX purified from the pig milk). This amount was chosen because it is in the range of F.IX most sensitive to inhibitors. Bleed times were measured six hours later. As shown in FIG. 4, group 2 shows that this dose of hF.IX partially corrected the bleeding time (clotting occurred within 7-10 minutes). This clotting time is about twice as long as the 4-6 minutes clotting time of normal mice (see FIG. 7A), showing that 0.13 IU of functional hF.IX is a highly sensitive range of factor. Bleeding times in the immunized unfed F.IX hemophilia B mice (FIG. 4, group 3) were as long as those in mice not given factor (FIG. 4, group 1), showing that the antibodies elicited by a single immunization with hF.IX in CFA were highly inhibitory. However, the F.IX knock-out mice (hemophilia B mice) that were orally tolerized before immunization (FIG. 4, group 4) showed little evidence of inhibitors, as their bleeding times were only slightly longer than those of infused mice that had not been immunized.

These results demonstrate that although orally tolerized mice produce antibodies when immunized with a very strong adjuvant, these antibodies do not lead to clinical resistance to hF.IX infusion. Therefore, the antibodies may be specific for denatured forms of the factor that occur in the adjuvant mixture and on ELISA plates, but the antibodies are not inhibitory to the native form of hF.IX in vivo.

EXAMPLE 4

Casein Oral Tolerance

This example describes the methods used to determine if sheep would develop oral tolerance to casein using the methods described in EXAMPLES 1 and 2. Similar methods can be used to test any antigen of interest, such as F.VIII, F.IX, protein C, or insulin, in any animal/subject of interest.

Lambs were raised on sheep or cow milk. After 3-4 months, lambs were immunized with 0.5 mg sheep casein in CFA. Three and six weeks later, lambs were boosted with 0.5 mg casein in incomplete Freund's adjuvant (IFA) (Sigma). Two months after the last immunization, peripheral blood mononuclear cells (PBMCs) were assayed for proliferation in the presence of titrated doses of sheep casein. Sheep PBMCs were isolated by centrifugating the blood through a lymphoprep gradient. Cells layered on the lymphoprep were collected and cultured in vitro in 96 well plates for four days in the presence of casein. Proliferation was measured by pulsing the cells with tritiated thymidine during the last eight hours of the culture and reading the results on a beta plate counter.

To measure casein-specific IgG in serum, maleic anhydride activated polystyrene plates were coated with sheep casein (10 µg/ml) for 30 minutes at 37° C. and blocked with PBS 1% BSA (bovine serum albumin) for 30 minutes. After discarding the blocking buffer and five washes, serum samples (⅒ diluted) were added into the wells and incubated for two hours. The plates were subsequently washed, and horseradish peroxidase (HRP) conjugated rabbit anti-sheep IgG (clone N126E, Southern Biotechnology Associates) was added and incubated for two hours, followed by TMP for color development, and plates subsequently read on an ELISA plate reader.

As shown in FIGS. 5A-5C, oral tolerance occurred in sheep. PBMCs from lambs that drank their mother's milk (sheep milk) did not proliferate in vitro to a sheep milk protein, casein, upon immunization as young adults (FIG. 5A). In contrast, lambs that were fostered on cow's milk showed a vigorous proliferative response (FIG. 5B). In addition, orally tolerized lambs failed to make antibodies to casein (FIG. 5C).

EXAMPLE 5

Orally Administered Clotting Factors Remain Functional

Having demonstrated that oral tolerance to several different antigens can be achieved, it was then demonstrated that the antigen remained functional after passing through the digestive system into the bloodstream. This example describes methods that were used to test the functionality of F.VIII and F.IX after they were orally administered. Similar methods can be used to identify a therapeutically effective amount of clotting factor necessary to increase hemostasis in a subject, such as in a hemophiliac.

Factor IX

Normal B10.A mice were fed either 0.5 ml of human F.IX in transgenic pig milk (which contained about 2.5 g/L of human F.IX; see Van Cott et al. 1999. Genet. Anal. 15:155-60) or water alone. One hour after feeding, plasma was obtained from the mice and added to sheep T cells that are reactive against human F.IX, to determine if the plasma could stimulate the sheep PBMCs. Sheep T cells reactive against human F.IX were generated by immunizing sheep with human F.IX (100 µg) in CFA. PBMC from these sheep proliferate in a dose-dependent manner to purified human F.IX in vitro (FIG. 4A, dotted line) and therefore can be used to measure the amounts of human F.IX in blood samples. The plasma was diluted from about 1:10 and decrease in 10-fold dilutions down to $1:10^7$. Cells were cultured for four days in 96 well plates and pulsed with tritiated thymidine the last eight hours of the culture. As a control, sheep T cells were cultured in the presence of purified human F.IX.

Figure 6B:
FIGS. 6A and 6B are a graph and a dot plot, respectively, showing that oral feeding of transgenic pig milk containing F.IX results in the presence of F.IX in the blood.
Figure 6A:
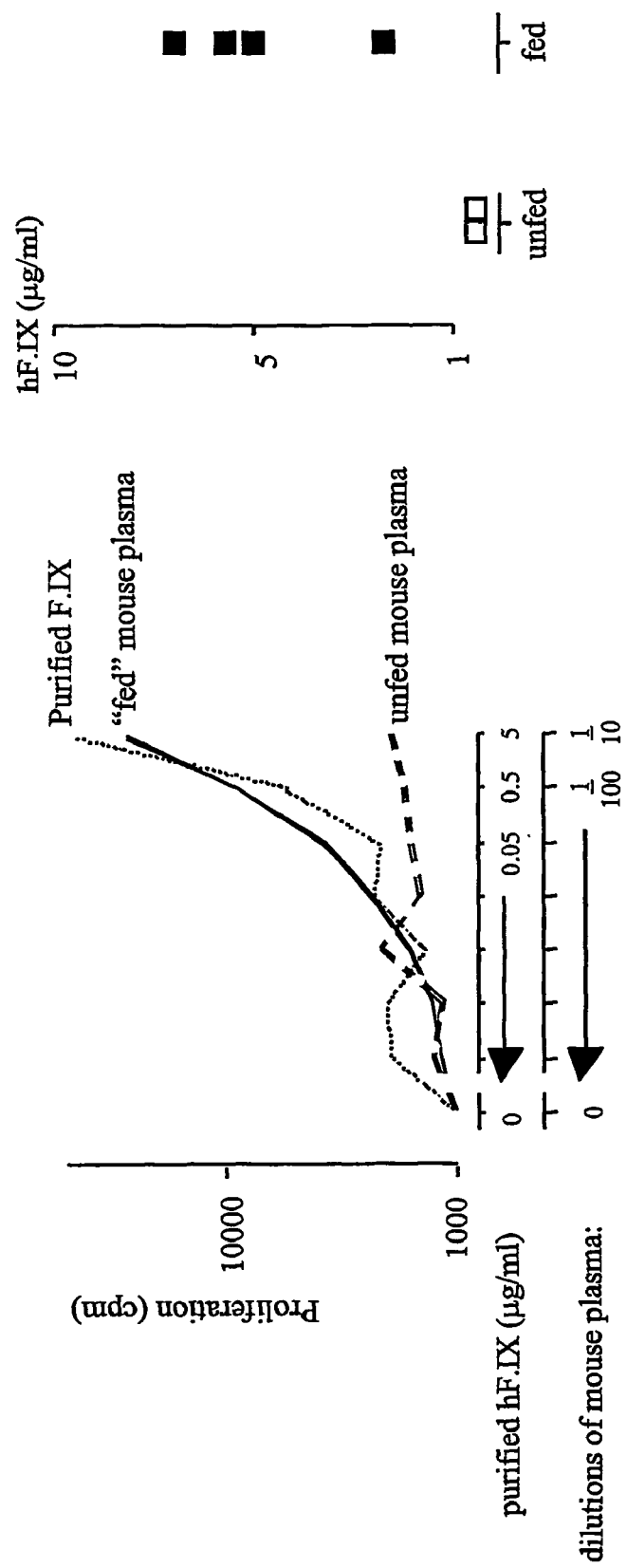

As shown in FIG. 6A, F.IX present in the pig milk passed into the plasma after feeding. Sheep PBMC responded strongly to the fed mouse plasma (FIG. 6A, solid line), but not to plasma from unfed mice (FIG. 6A, bottom dashed line). It was determined that the fed mouse plasma contained about 6.7 ug/ml of human F.IX, indicating that about 0.1% of the fed F.IX entered the circulation. This result was confirmed by a sandwich ELISA to detect human F.IX in plasma after feeding (FIG. 6B). For the ELISA assay, 96 well flat-bottom ELISA plates from PIERCE (Rockford, Ill.) were coated with sheep-anti-human F.IX polyclonal antibody (Cedarlane Laboratories, Ontario, Canada), then blocked with 10% BSA. Mouse plasma were diluted from ⅒ to ¹⁄₁₀,₀₀₀ and added into the wells, incubated for two hours, washed with wash buffer, and then HRP-conjugated polyclonal goat anti-human F.IX antibodies (Cedarlane Laboratories) added for two hours. Color was developed by adding TMP, and results obtained using an ELISA plate reader. As shown in FIG. 6B, the amount of F.IX in the blood of F.IX-fed mice was similar when measured by ELISA to that measured by the PBMC (FIG. 6A) and that most F.IX passes into the circulation as intact protein.

To determine if fed human F.IX retains its native form and functional ability to treat bleeding episodes, F.IX-containing transgenic pig milk (1.25 mg F.IX) was fed to hemophilia B mice (a F.IX knock-out obtained from Dr. Katherine High, Children's Hospital of Philadelphia; approximately 20 g in weight) over a period of two months every other day and the effect on a bleeding defect determined. Bleeding time was measured by cutting the tip of the tail and waiting for it to clot. Normal mice clot in about four minutes (FIG. 7A, open squares). In contrast, hemophilia B mice do not stop bleeding (FIG. 7A, open circles) and the tail tip is cauterized to stop bleeding after fifteen minutes. As shown in FIG. 7A, oral administration of F.IX immediately corrected the bleeding defect (FIG. 7A, closed circles). In addition, this result is sustained for a period of at least two months (FIG. 7B), indicating that anti-F.IX antibodies are not being generated, which allows the F.IX to remain functional. Therefore, oral administration of human F.IX is an effective treatment for bleeding, and does not induce inhibitory immunity, even following a long-term treatment.

Factor VIII

To demonstrate that hemophilia A, caused by the lack of functional F.VIII, could also be treated by oral administration of factor, milk from a transgenic pig engineered to secrete hF.VIII was fed to F.VIII knock-out mice. However, this treatment had no effect on oral tolerance or on clotting times. It was possible that the dose of F.VIII was too low, since this particular transgenic strain of pig does not produce large quantities of F.VIII (Paleyanda et al. *Nature Biotech.* 15:971-5, 1997). Another explanation is that hF.VIII is almost 8 times larger than F.IX, with a molecular weight of nearly 240,000 kDa, which might make it difficult to pass into the bloodstream.

To distinguish between these possibilities, the studies were repeated with commercially available F.VIII (Baxter) purified from human plasma (Red Cross Holland labs, Rockville, Md.). hF.VIII (100 µg) was added to 0.5 ml of water or cow's milk and fed to hemophilia A mice by gavage. Bleeding time was assayed 45 minutes later. As shown in FIG. 8A, the bleeding time was corrected in hemophilia A mice fed hF.VIII either in water or milk. Therefore, sufficient hF.VIII passes into the bloodstream in native form to function as a clotting factor, despite the size and complexity of the molecule.

To determine whether hF.VIII might be passing through small lacerations created by the gavage process, F.VIII was fed to the mice in a more physiologic way, by dissolving 400 µg hF.VIII in 8 ml of commercial half cream/half milk and offering this to the mice in petri dishes. Three mice drank about 12 ml of this mixture in about 2 hours, delivering about 200 µg to each mouse daily. Bleeding time was assayed 45 minutes later. As shown in FIG. 8B, this method was also an effective method to treat the bleeding disorder.

To demonstrate that feeding hF.VIII induces oral tolerance, hF.VIII was fed to hemophilia A mice (F.VIII knock-out mice) in commercial half and half (600 µg F.VIII/12 ml of half and half) daily for eight days. Control mice were fed plain half and half. On day 10, mice were bled to determine the bleeding time (FIG. 8C, pre-imm), then immunized with hF.VIII in CFA as described in the Examples above. Seven days later, all mice were fed hF.V111-containing half-and-half to determime if immunization-induced inhibitors would prevent the oral dose of F.VIII from functioning as a clotting factor.

A single immunization did not inhibit the function of the orally administered factor in previously orally tolerized mice (FIG. 8C, closed circles), but did cause a loss of function in previously unfed controls (FIG. 8C, open circles). The test group was fed every other day, starting again from day 19 for an additional 7 days. Mice were then boosted with hF.VIII in IFA, and again assayed for bleeding time 7 days later. Even after this second immunization with a strong adjuvant, the previously orally tolerized mice exhibited normal bleeding times, while the un-tolerized controls did not.

The mice were then sacrificed and checked for antibodies to F.VIII. Control mice had high levels of IgG2a antibodies (FIG. 8D, open circles), which is consistent with their inability to respond to treatment with hF.VIII. In contrast, the orally tolerized mice had barely detectable levels of IgG2a (FIG. 8D, closed circles). Although orally tolerized mice did have some IgG1 antibodies specific for hF.VIII, after immunization (FIG. 8C), these antibodies behaved like the similar antibodies in orally tolerized wild type mice. These antibodies are not inhibitors, as they did not affect the bleeding time (FIG. 8C).

This is the first demonstration that missing clotting factors can be demonstrated in the circulation of hemophiliac mice as early as 45 minutes after feeding, and that the orally-fed clotting factors are functional, as demonstrated by correction in bleeding time. Although it is commonly assumed that dietary proteins are digested completely to free amino acids within the lumen of the gastrointestinal tract and that only trace amounts of macromolecular fragments enter the circulation having no clinical relevance, there is mounting evidence that suggests the opposite. The most compelling evidence showing that intact proteins or macromolecular fragments are absorbed is provided by the demonstration of antibodies to many food proteins that occur in the circulation of healthy individuals and experimental animals. For example, 5% of recombinant human erythropoietin (about 40 kDa) fed to 10-day old rats was demonstrated in the serum as early as one hour after feeding (Miller-Gilbert et al. 2001. *Pediatr. Res.* 50:261-7). Serum erythropoietin levels remained steady for up to 6 hours as opposed to the rapid peak and fall observed after intravenous administration. Although orally administered erythropoietin showed functional activity in Hess mice by stimulation erythropoiesis, this could have been due to the stimulation of erythropoietin receptors on the enterocytes within the gastrointestinal tract.

Similarly, gastrointestinal absorption of intact TGFβ1 was demonstrated after administration (by gavage) of radiolabeled TGFβ into the stomachs of 5-day old pups (Letterio et al. 1994. *Science* 264:1936-8). Although the neonatal gut is very permeable to intact proteins, similar results were observed in adult animals. In mice, rats, and fish fed ovalbumin, casein or HRP respectively, between 0.005 to 0.7% of the total fed amount was measured in the circulation either by ELISA or Western analysis (Gonnella et al. 2001. *J. Immunol.* 166:4456-64). Interestingly, the amount of antigen that passed into the circulation was much higher in B-cell deficient mice compared to wild type controls, suggesting that the lack of M cells does not affect the transport of proteins across the gut.

Although both intravenous and oral administration of proteins results in detectable serum levels, antigen entry through the mucosa provides certain benefits. First, pharmacokinetically, as opposed to a rapid rise and decline as seen after intravenous administration, oral administration provides relatively steady levels of the protein. Second, immunologically, it generates a gut-oriented immunity, which avoids inhibitory or rejecting antibodies. Therefore, feeding F.VIII and F.IX in hemophilia A and B, respectively, is a simple, noninvasive and effective method of treating hemophilia. In addition, it induces oral tolerance, avoiding the generation of inhibitory antibodies and a vigorous T-cell response against missing clotting factors.

EXAMPLE 6

Comparison of Oral Administration of Clotting Factors in Water and Milk

To determine if the presence of milk was critical to achieve oral tolerance and maintain proper function of the clotting factor, the administration of F.VIII or F.IX in milk and water was compared.

Purified F.VIII from human serum was orally administered to hemophilia A mice (F.VIII knock out; Dr. Kang, U. of Iowa,) in cow's milk or in water. Mice were fed 100 μg of F.VIII (antihemophilic factor, Baxter, Deerfield, Ill.) by gavage in 0.5 ml of water or cow's milk. Bleeding time was measured as described above, 45 minutes after feeding. As shown in FIG. 8A, feeding F.VIII derived from human plasma that is added into cow's milk or water corrects bleeding time in hemophilia A mice. Therefore, the presence of milk when orally administering F.VIII is not critical.

To determine if the presence of milk was critical to achieve oral tolerance to F.IX, normal B10.A mice were fed with low (10-20 μg F.IX/feed) or high (2500 μg F.IX/feed) does of human F.IX in pig milk or as purified plasma-derived human F.IX (Sigma) reconstituted in water (10-20 μg F.IX/feed) every other day for a total of five feeds. Control mice were fed no F.IX. Two days later, mice were immunized with 0.5 μg human F.IX emulsified in CFA at the base of the tail. Seven days later, the amount of T cell proliferation was determined using the methods described in EXAMPLE 1. As shown in FIGS. 9A and 9B, mice fed as little as 20 μg F.IX in milk (FIG. 9A) were almost completely unresponsive, while T cells from mice fed with F.IX in water (FIG. 9B) retained a small amount of activity (about 3% of unfed controls). However, administration of F.IX in water or milk resulted in better oral tolerance than no administration of F.IX.

In summary, a dose of 100 μg F.VIII/20 g body weight (about 5 mg/kg), orally administered every day (or every other day), can be used to increase hemostasis, thus treating hemophilia A. In addition, a dose of 1 mg F.IX/20 g body weight (about 50 mg/kg), orally administered every day (or every other day), is expected to increase hemostasis thus treating hemophilia B. However, it is possible that lower doses can be used, or that higher doses may be required in a particular subject, in order to obtain a successful treatment of hemophilia.

EXAMPLE 7

Determination of Parameters for Low Dose Oral Tolerance

To identify optimal conditions to achieve low dose oral tolerance to human F.IX delivered in transgenic pig milk, the following methods can be used. Similar methods can be used to determine the conditions for other antigens, including F.VIII, insulin, and protein C, in humans.

Lambs can be used as an experimental model. Sheep are an outbred species and, like humans (but unlike mice), their immune system becomes functional during the last trimester of pregnancy. They are also easier than mice to bottle-feed. The architecture of sheep intestines during the first 24-48 hours of life is designed to collect maternal antibodies from colostrum, with very high levels of Fc receptors that have a half-life of about 24 hours. Therefore, feeding of F.IX milk is started 48 hours after birth, when the gut has settled.

Lambs are fed 0.3 mg F.IX/kg of animal/day, the amount of protein shown to induce low dose tolerance in 20 g mice (FIGS. 1A-1C). The effective dose range in mice is 0.001 to 0.1 mg for OVA (0.05-5 mg/kg) and 0.003 to 0.1 mg/day for F.IX (0.15-0.5 mg/kg). Lambs are fed daily for three weeks with sheep milk supplemented with pig milk containing human F.IX (see EXAMPLE 5). A parallel control group of lambs is supplemented with normal pig milk containing no human F.IX. Milk is collected, frozen immediately, and thawed just before use. Experiments with mice demonstrate that continuous daily feeding is the most effective way of inducing oral tolerance.

Sheep can be immunized as early as two weeks of age. At three weeks of age, half the lambs are immunized with F.IX in CFA after the feedings are completed and then boosted two weeks later with F.IX in IFA. A dose of 100 μg human F.IX is sufficient to prime young ewes for a subsequent proliferative and antibody response. Lambs are tested for various types of immunity against F.IX after each immunization.

Three assays can be used to detect immune responses against F.IX. First, the amount of peripheral blood mononuclear cell proliferation can be determined. One week and two weeks after immunization, 10-20 ml of venous blood is collected by jugular venipuncture, the mononuclear cells fractionated using Percoll gradients and subsequently cultured in vitro in the presence of titrated amounts of F.IX, and assay for proliferation as described in EXAMPLES 1, 2 and 4.

Second, serum F.IX specific antibody titers can be determined. From each blood sample collected, serum is extracted. Dilutions of the serum are added to ELISA plates (Pierce) coated with human F.IX (10 μg/ml). After a two hour incubation, the plates are washed with wash buffer, then incubated with polyclonal HRP-conjugated goat anti-human F.IX antibodies (Cedarlane Laboratories) for two hours. For color development TMP is added and then the plates are read in an ELISA plate reader. Antibodies of different classes can be identified using the sandwich ELISA method described in EXAMPLES 4 and 5.

Third, a factor IX inhibitor assay (Bethesda Assay) can be conducted. This functional assay measures the amount of inhibitor antibody in serum. The Bethesda assay is an in vitro functional assay performed by mixing plasma containing unknown amounts of inhibitors (test plasma) with normal plasma to determine how the test plasma prolongs the APTT of the normal plasma.

Lambs fed human F.IX should not generate a strong specific proliferative response, and should not develop antibodies against F.IX. If antibodies are produced, they will be of the secretory IgA type and will not be inhibitory against F.IX.

It is possible that the determined effective dose in sheep or other subjects (such as humans) may differ from that in mice. If feeding 0.3 mg/kg/day F.IX does not result in oral tolerance, experiments can be repeated using a titration of higher and lower doses of F.IX, to determine the appropriate dose. In addition, it can also be determined whether feeding during the first 48 hours of life can enhance oral tolerance.

EXAMPLE 8

Determination of Parameters for High Dose Oral Tolerance

To determine parameters that are helpful to achieve optimal high dose oral tolerance to human F.IX delivered in transgenic pig milk, the following methods can be used. Similar methods can be used to determine the parameters for other antigens, including F.VIII, insulin, and protein C.

Although low dose tolerance induces remarkable reductions in cellular responses, it may allow for some antibody production. Though antibodies are unlikely to result in rejection of cells expressing a F.IX transgene, they may inhibit the secreted product. Therefore, tolerance can also be induced by feeding high doses of F.IX. This approach has not been feasible in the past because of the extraordinarily high cost of purified F.IX. However, induction of oral tolerance does not require purified antigen. As experiments in sheep illustrate (FIGS. 5A-5C), newborns become tolerant of milk proteins even when the proteins are given as mixtures in normal milk. The tolerizing ability of unpurified transgenic pig milk containing 2.5 g/L F.IX (see EXAMPLE 5) in the native situation where piglets feed continuously is tested.

Non-transgenic piglets are fostered onto transgenic mothers and allowed to drink ad libitum until weaned. A control group of foster littermates is fostered onto non-transgenic control mothers. Two days after the animals are weaned, half of the piglets in each group are subcutaneously immunized with F.IX (0.1 mg) in CFA and two weeks later, boosted with F.IX in IFA. Half of the piglets will be un-immunized as controls. One and two weeks after each immunization various classes of immunity will be determined as described above in EXAMPLE 7.

Piglets that drank F.IX containing milk from transgenic mothers are expected to be tolerant to FIX. This tolerance is tested by subsequently immunizing these piglets to human F.IX in CFA as described in the examples above. Tolerance is achieved if there is decreased antibody formation and T cell proliferation in these piglets compared to piglets fostered onto a non-transgenic mother using the methods described in the examples above.

EXAMPLE 9

Oral Tolerance in Hemophiliac Puppies

This example describes procedures that can be used to develop oral tolerance to clotting factors in hemophiliac puppies. The method specifically outlines methods for testing tolerance to F.IX in hemophiliac B puppies, but those skilled in the art will understand from the teachings herein that similar methods can be used to test for tolerance to F.VIII in hemophiliac A puppies, or for tolerance to any antigen in any subject having an antigen-deficiency disease.

A canine model of hemophilia A is available (Giles et al. 1982. *Blood* 60:727-30; and Giles et al. 1984. *Blood* 63:451-6). Hemophilia A was diagnosed in a miniature Schnauzer dog and inbreeding and crossbreeding produced 16 hemophilic animals. Five animals developed potent antibodies to canine F.VIII. In each case, the antibodies recognize both canine and human, but not porcine F.VII. Following inhibitor development, infusion of canine cryoprecipitate was hemostatically ineffective and F.VIII recovery at 30 minutes is negligible.

Two canine models of hemophilia B are available. In the Chapel Hill dog colony, hemophilia B is due to a missense mutation, and inhibitor formation in response to canine plasma or gene therapy maneuvers is relatively uncommon (Evans et al. 1989. *Proc. Natl. Acad. Sci. U S A*. 86:10095-9). However, for the Auburn dog colony, where disease is due to a small deletion that results in an early stop codon (Mauser et al. 1996. *Blood*. 88:3451-5), inhibitor formation is more frequent. In both types of mutations, inhibitors to canine F.IX can be induced by various means including repeated injection of purified canine F.IX, or injection of vector expressing canine F.IX. The rise in inhibitor antibodies correlates with fall of plasma F.IX levels (Herzog et al. 1999. *Nat. Med.* 5:56-63). Both colonies of dogs readily form inhibitory antibodies following infusion of human F.IX.

To assess the effect of oral tolerance on the development of clotting factor inhibitors after immunization, canine models for hemophilia are used. F.IX is administered orally to normal puppies and to puppies with hemophilia B (Auburn dog colony) and their spontaneous immune responses against F.IX analyzed.

The optimal feeding dose of F.IX found to prevent development of inhibitory antibodies is used (see EXAMPLES 5-8). Normal and hemophilia B puppies are divided into two groups: one group is fed F.IX-containing transgenic pig milk, and the other group fed non-transgenic pig milk to serve as controls. Puppies are fed for six weeks until they are fully weaned.

The puppies are then infused with 50 IU/kg human F.IX intravenously daily for two weeks, starting two days after weaning, or earlier if necessary to control bleeding. The generation of inhibitor antibodies after repeated intravenous administration of human F.IX has been well established in the canine model (Evans et al. 1989. *Proc. Natl. Acad. Sci. U S A.* 86:10095-9). The course of the disease is followed, periodically assaying for inhibitory antibodies using the Bethesda assay (see EXAMPLE 7), especially after F.IX infusions due to bleeding episodes.

PBMC proliferation and serum antibody titers against F.IX are also compared between control and experimental animals, as described in EXAMPLE 4, except that the in vitro assays are modified to suit canine cells. For example, IMDM plus canine serum is a superior medium for canine proliferation assays whereas RPM plus fetal calf serum serves well for sheep.

It is expected that the intact antigen will gain access to the bloodstream after feeding, as was obtained for F.IX in mice (EXAMPLE 5). To test for F.IX in plasma samples from F.IX-fed hemophilia B and normal puppies, methods described in EXAMPLE 5 are used.

To determine if the F.IX antigen remains functional after oral administration, a functional assay is performed. For example, an APTT assay which measures the intrinsic coagulation activity of the plasma can be used.

Therefore, in addition to orally tolerizing the immune system, it is determined whether small amounts of functional F.IX can reach the blood and help prevent bleeding episodes, thus increasing hemostasis.

It is expected that oral administration of F.IX by feeding will induce oral tolerance and prevent the development of inhibitory antibodies, as well as remain functional in the blood, and therefore increase hemostasis and serve as a treatment for hemophilia.

EXAMPLE 10

Oral Administration Followed by In Vivo Gene Expression

To demonstrate that administration and subsequent expression of a F.IX-containing transgene can be used to treat hemophilia, adeno-associated vectors containing a F.IX gene can be used.

After orally tolerizing puppies to F.IX as described in EXAMPLE 9, adeno-associated viral vectors are used to introduce the human F.IX gene into hemophiliac puppies orally tolerized to human F.IX to increase hemostasis. Similar methods can be used in human hemophiliacs.

Methods for generating an introducing transgenes into a subject are well known in the art. In addition, viral vectors for introducing a clotting factor into a subject are known. Examples of methods and vectors that can be used to introduce a clotting factor into a subject, include, but are not limited to those disclosed in: Stein et al., 2001. *Mol. Ther.* 3:850-6; Miller et al., 2001. *N. Engl. J. Med.* 344:1782-4; Emilien et al., 2000. Clin. Lab. Haematol. 22:313-23; Andrews et al., 2001. *Mol. Ther.* 3:329-36; Fabb et al., 2000. *Curr. Opin. Mol Ther.* 2:601-6; and Lillicrap, 2000. *Haematologica* 85(10 Suppl): 108-12, as well as other documents cited herein.

Following administration of the vector, F.IX levels in serum, as well as immunity to F.IX, are monitored as described in EXAMPLES 5 and 7, over a period of one year or until the factor disappears, whichever comes first.

It is expected that oral administration of a clotting factor by feeding will induce oral tolerance and prevent the development of inhibitory antibodies, such that when the factor is subsequently expressed recombinantly in the subject, the recombinant protein will not be inactivated by anti-clotting factor antibodies. This will result in functional clotting factor in the blood, and therefore increase hemostasis and serve as a treatment for hemophilia.

EXAMPLE 11

Oral Tolerance and Treatment in Humans

This example describes methods that can be used to induce tolerance to F.IX in a human hemophiliac. Similar methods can be used to induce oral tolerance to any antigen of interest in a human subject, for example F.VIII, insulin and protein C.

Among hemophilia patients that form inhibitors, the incidence of patients with large deletions is known (deletion/total inhibitor production=0.5). However, due to the cost of widespread genetic screening, and the lack of practical consequence to the management of hemophilia patients, the incidence of inhibitor producers among those with large deletions is not known (inhibitor production/large deletions).

The patient group most likely to benefit from treatment are children that have no F.IX, thus making them particularly prone to making inhibitors. After determining the F.IX levels in plasma of a hemophiliac child, patients having undetectable levels are further tested to determine whether they have a large F.IX deletion. From this study, the incidence of inhibitor producers among those who have large deletions can be determined.

From studies on hemophiliac puppies, patients with large deletions are believed to be particularly prone to making inhibitors and thus particularly at risk of becoming refractory to replacement therapy.

Hemophiliac children are orally tolerized by oral administration (feeding) of F.IX-containing transgenic milk. Alternatively, purified F.IX can be administered orally in any medium suitable for oral administration, including water.

The immune response to F.IX during the course of the disease is monitored as described in EXAMPLE 7. In addition, the amount of functional F.IX in the blood, the formation of antibodies against F.IX and PBMC proliferation are monitored as described above.

In addition, hemostasis is monitored, using an APTT assay described in EXAMPLE 7 or a bleeding time assay. Treatment is successful if hemostasis is increased relative to hemostasis prior to oral administration of the clotting factor, or relative to untreated hemophiliacs.

EXAMPLE 12

Oral Tolerance Followed by In Vivo Gene Expression

As an alternative to continually orally administering a clotting factor to a subject to increase hemostasis, once oral tolerance is achieved, long term treatment of the clotting disorder can be achieved by expressing the deficient clotting factor in vivo. Similar methods can be used to treat any antigen-deficiency disease.

The present disclosure provides methods of expressing a protein in a cell or tissue in vivo. In one embodiment, transfection of the cell or tissue occurs in vitro. In this example, the cell or tissue (such as a graft) is removed from a subject and then transfected with an expression vector containing a cDNA encoding the protein of interest. The transfected cells will produce functional protein and can be reintroduced into the subject. In another embodiment, a nucleic acid encoding the protein of interest is administered to a subject directly, and transfection occurs in vivo.

The methods disclosed herein can be used to treating a subject with an antigen-deficiency disease such as a subject having hemophilia A or B. Such a method would increase hemostasis (decrease blood clotting time) in hemophiliacs or subjects having other defects in blood clotting.

The scientific and medical procedures required for human cell transfection are now routine. The public availability of numerous protein and cDNA sequences allows the development of human (and other mammals) in vivo gene expression based upon these procedures. Immunotherapy of melanoma patients using genetically engineered tumor-infiltrating lymphocytes (TILs) has been reported by Rosenberg et al. (*N. Engl. J. Med.* 323:570-8, 1990). In that study, a retrovirus vector was used to introduce a gene for neomycin resistance into TILS. A similar approach may be used to introduce a clotting factor cDNA into hemophiliacs.

In some embodiments, a method of treating subjects which under express a functional protein, or in which greater functional protein expression is desired, is disclosed. These methods can be accomplished by introducing a gene coding for the desired protein into a subject. A general strategy for transferring genes into donor cells is disclosed in U.S. Pat. No. 5,529,774, incorporated by reference. Generally, a gene encoding a protein having therapeutically desired effects is cloned into a viral expression vector, and that vector is then introduced into the target organism. The virus infects the cells, and produces the protein sequence in vivo, where it has its desired therapeutic effect. Zabner et al. (*Cell* 75:207-16, 1993).

It may only be necessary to introduce the genetic or protein elements into certain cells or tissues. However, in some instances, it may be more therapeutically effective and simple to treat all of a subject's cells, or more broadly disseminate the vector, for example by intravascular (i.v.) administration.

The nucleic acid sequence encoding at least one therapeutic agent, such as a clotting factor, is under the control of a suitable promoter. Suitable promoters which may be employed include, but are not limited to, the gene's native promoter, retroviral LTR promoter, or adenoviral promoters, such as the adenoviral major late promoter; the CMV promoter; the RSV promoter; inducible promoters, such as the MMTV promoter; the metallothionein promoter; heat shock promoters; the albumin promoter; the histone promoter; the α-actin promoter; TK promoters; B19 parvovirus promoters; and the ApoAI promoter. However the scope of the disclosure is not limited to specific foreign genes or promoters.

The recombinant nucleic acid can be administered to the subject by any method which allows the recombinant nucleic acid to reach the appropriate cells. These methods include injection, infusion, deposition, implantation, or topical administration. Injections can be intradermal or subcutaneous. The recombinant nucleic acid can be delivered as part of a viral vector, such as avipox viruses, recombinant vaccinia virus, replication-deficient adenovirus strains or poliovirus, or as a non-infectious form such as naked DNA or liposome encapsulated DNA, as further described in EXAMPLE 13.

EXAMPLE 13

Viral Vectors for In Vivo Gene Expression

Adenoviral vectors include essentially the complete adenoviral genome (Shenk et al., Curr. Top. Microbiol. Immunol. 111:1-39, 1984). Alternatively, the adenoviral vector is a modified adenoviral vector in which at least a portion of the adenoviral genome has been deleted. In one embodiment, the vector includes an adenoviral 5' ITR; an adenoviral 3' ITR; an adenoviral encapsidation signal; a DNA sequence encoding a therapeutic agent; and a promoter for expressing the DNA sequence encoding a therapeutic agent. The vector is free of at least the majority of adenoviral E1 and E3 DNA sequences, but is not necessarily free of all of the E2 and E4 DNA sequences, and DNA sequences encoding adenoviral proteins transcribed by the adenoviral major late promoter. In another embodiment, the vector is an adeno-associated virus (AAV) such as described in U.S. Pat. No. 4,797,368 (Carter et al.) and in McLaughlin et al. (J. Virol. 62:1963-91, 1988) and AAV type 4 (Chiorini et al. J. Virol. 71:6823-33, 1997) and AAV type 5 (Chiorini et al. J. Virol. 73:1309-19, 1999)

Such a vector can be constructed according to standard techniques, using a shuttle plasmid which contains, beginning at the 5' end, an adenoviral 5' ITR, an adenoviral encapsidation signal, and an E1a enhancer sequence; a promoter (which may be an adenoviral promoter or a foreign promoter); a tripartite leader sequence, a multiple cloning site (which may be as herein described); a poly A signal; and a DNA segment which corresponds to a segment of the adenoviral genome. The DNA segment serves as a substrate for homologous recombination with a modified or mutated adenovirus, and may encompass, for example, a segment of the adenovirus 5' genome no longer than from base 3329 to base 6246. The plasmid can also include a selectable marker and an origin of replication. The origin of replication may be a bacterial origin of replication. A desired DNA sequence encoding a therapeutic agent can be inserted into the multiple cloning site of the plasmid.

Examples of vectors which can be used to practice the methods disclosed herein include those disclosed in: WO 95/27512 to Woo et al.; WO 127303 to Walsh et al.; U.S. Pat. No. 6,221,349 to Couto et al.; U.S. Pat. No. 6,093,392 to High et al.

EXAMPLE 14

Production of Sequence Variants

Disclosed herein methods for treating antigen-deficiency diseases by oral administration of the appropriate antigen or protein. It is understood by those skilled in the art that use of non-native antigen sequences (such as polymorphisms, fragments, or variants) can be used to practice the methods of the present disclosure, as long as the distinctive functional characteristics of the antigen are retained. For example, F.IX or F.VIII variants can be used to practice the methods disclosed herein if they retain their ability to increase hemostasis. This activity can readily be determined using the assays disclosed herein, for example those described in EXAMPLES 5 and 9. In yet other embodiments, F.IX or F.VIII has the distinct characteristic of being reduced in patients suffering from hemophilia.

This disclosure facilitates the use of DNA molecules, and thereby proteins, derived from a native protein but which vary in their precise nucleotide or amino acid sequence from the native sequence. Such variants can be obtained through standard molecular biology laboratory techniques and the sequence information disclosed herein.

DNA molecules and nucleotide sequences derived from a native DNA molecule can also be defined as DNA sequences which hybridize under stringent conditions to the DNA sequences disclosed, or fragments thereof. Hybridization conditions resulting in particular degrees of stringency vary depending upon the nature of the hybridization method and the composition and length of the hybridizing DNA used. Generally, the temperature of hybridization and the ionic strength (especially the $Na^+$ concentration) of the hybridization buffer determines hybridization stringency. Calculations regarding hybridization conditions required for attaining particular amounts of stringency are discussed by Sambrook et al. (Molecular Cloning: A Laboratory Manual, Cold Spring Harbor, N.Y., 1989, Chapters 9 and 11), herein incorporated by reference. Hybridization with a target probe labeled with [$^{32}$P]-dCTP is generally carried out in a solution of high ionic strength such as 6×SSC at a temperature that is about 5-25° C. below the melting temperature, $T_m$. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na phosphate, 5 mM EDTA, pH 7.4) at 25-30° C. are suitable for allele-specific probe hybridizations.

The degeneracy of the genetic code further widens the scope of the present disclosure as it enables major variations in the nucleotide sequence of a DNA molecule while maintaining the amino acid sequence of the encoded protein. For example, the amino acid Ala is encoded by the nucleotide codon triplet GCT, GCG, GCC and GCA. Thus, the nucleotide sequence could be changed without affecting the amino acid composition of the encoded protein or the characteristics of the protein. Based upon the degeneracy of the genetic code, variant DNA molecules may be derived from a cDNA molecule using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are also comprehended by this disclosure.

Clotting factor variants, fragments, fusions, and polymorphisms will retain the ability to increase hemostasis, as determined using the assays disclosed herein, for example by performing an APTT assay (EXAMPLE 9) or a bleeding time assay. Variants and fragments of a protein may retain at least 70%, 80%, 85%, 90%, 95%, 98%, or greater sequence identity to a protein amino acid sequence and maintain the functional activity of the protein as understood by those in skilled in the art. Examples of clotting factor variants, include, but are not limited to those disclosed in U.S. Pat. No. 6,221,349 to Couto et al.; U.S. Pat. No. 4,877,614 to Andersson et al.; EP 770396 to Zimmermann et al.; U.S. Pat. No. 6,093,392 to High et al.; and EP 0294910 to van Ooyen et al.

EXAMPLE 15

Recombinant Expression of Proteins

With publicly available cDNA and corresponding amino acid sequences, as well as the disclosure herein of variants, fragments and fusions thereof, the expression and purification of any publicly known protein by standard laboratory techniques is enabled. The purified protein can be used for patient therapy. For example, mammals that produce recombinant F.VIII or F.IX in their milk are known (see U.S. Pat. No. 5,880,327 to Lubon et al. and Van Cott et al. 1999. *Genet. Anal.* 15:155-60, respectively), and can be used to practice the methods disclosed herein. However, one skilled in the art will understand that the orally administered clotting factor can be produced in any cell or organism of interest, and purified prior to administration to a subject, as an alternative to feeding the subject milk containing the recombinant clotting factor.

Methods for producing recombinant proteins are well known in the art. Therefore, the scope of this disclosure includes recombinant expression of any antigen/protein. For example, see U.S. Pat. No. 5,342,764 to Johnson et al.; U.S. Pat. No. 5,846,819 to Pausch et al.; U.S. Pat. No. 5,876,969 to Fleer et al. and Sambrook et al. (*Molecular Cloning: A Laboratory Manual*, Cold Spring Harbor, N.Y., 1989, Ch. 17, herein incorporated by reference).

In addition, methods for producing recombinant clotting factors are known, for example as disclosed in EP 0294910 (and references therein); EP 0160457; EP 0253455; EP 0150735; U.S. Pat. No. 6,221,349 to Couto et al.; U.S. Pat. No. 5,804,420 to Chan et al. and U.S. Pat. No. 4,770,999 to Kaufman et al.

EXAMPLE 16

Peptide Modifications

Orally administered proteins can be modified using a variety of chemical techniques to produce derivatives having essentially the same activity as the unmodified peptides, and optionally having other desirable properties. For example, carboxylic acid groups of the peptide, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chain can be converted to $C_1$-$C_{16}$ alkoxy or to a $C_1$-$C_{16}$ ester using well-recognized techniques. Phenyl and phenolic rings of the peptide side chain can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides disclosed herein to select and provide conformational constraints to the structure that result in enhanced stability. For example, a carboxyl-terminal or amino-terminal cysteine residue can be added to the peptide, so that when oxidized the peptide will contain a disulfide bond, generating a cyclic peptide. Other peptide cyclizing methods include the formation of thioethers and carboxyl- and amino-terminal amides and esters.

To maintain a functional peptide, particular peptide variants will differ by only a small number of amino acids from a peptide. Such variants can have deletions (for example of 1-3 or more amino acids), insertions (for example of 1-3 or more residues), or substitutions that do not interfere with the desired activity of the peptide. Substitutional variants are those in which at least one residue in the amino acid sequence has been removed and a different residue inserted in its place. In particular embodiments, such variants have amino acid substitutions of single residues, for example 1, 3, 5 or even 10 substitutions in a protein.

Peptidomimetic and organomimetic embodiments are also disclosed herein, whereby the three-dimensional arrangement of the chemical constituents of such peptido- and organomimetics mimic the three-dimensional arrangement of the peptide backbone and component amino acid sidechains in the peptide, resulting in such peptido- and organomimetics of a clotting factor having the ability to increase hemostasis. For computer modeling applications, a pharmacophore is an idealized, three-dimensional definition of the structural requirements for biological activity. Peptido-and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* (ed. Munson, 1995), chapter 102 for a description of techniques used in CADD.

EXAMPLE 17

Pharmaceutical Compositions and Modes of Administration

The pharmaceutically effective carriers useful herein are conventional. *Remington's Pharmaceutical Sciences*, by Martin, Mack Publishing Co., Easton, Pa., 15th Edition (1975), describes compositions and formulations suitable for pharmaceutical delivery.

Oral Administration of Antigens and Proteins

In an embodiment in which an antigen, such as a clotting factor, is administered to a subject, the antigen is delivered enterally, for example orally (e.g., by feeding), or rectally (e.g., by suppository). The present disclosure also provides pharmaceutical compositions which include a therapeutically effective amount of a clotting factor alone or with a pharmaceutically acceptable carrier. Furthermore, the pharmaceutical compositions or methods of treatment can be administered in combination (or separately) with one or more other therapeutic treatments, such as other agents that increase hemotasis. Embodiments of the disclosure comprising medicaments can be prepared with conventional pharmaceutically acceptable carriers, adjuvants and counterions as would be known to those of skill in the art.

The antigen can be administered in combination with at least one, for example one or more pharmaceutically effective carriers, such as a pharmaceutically and physiologically acceptable fluid. Examples of pharmaceutically effective carriers include, but are not limited to milk, water, physiological saline, balanced salt solutions, aqueous dextrose, sesame oil, glycerol, ethanol, combinations thereof, or the like, as a vehicle. The carrier and composition can be sterile, and the formulation suits the mode of administration. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder, but not a liposome also containing a protease inhibitor. For solid compositions (e.g., powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

The amount of antigen, such as a clotting factor, effective in the treatment of a particular disorder or condition, such as hemophilia, will depend on the nature of the disorder or condition, and can be determined by standard clinical techniques. In addition, in vitro assays can be employed to identify optimal dosage ranges (see EXAMPLES 7 and 8). The precise dose to be employed in the formulation will also depend on the seriousness of the disease or disorder, and should be decided according to the judgment of the practitioner and each subject's circumstances. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

Administration of Nucleic Acid Molecules

In an embodiment in which a nucleic acid is employed to allow expression of a nucleic acid in a cell, the nucleic acid is delivered intracellularly (e.g., by expression from a nucleic acid vector or by receptor-mediated mechanisms). In one embodiment, a nucleic acid encodes for an antigen, such as a clotting factor.

Various delivery systems for administering a nucleic acid are known, and include encapsulation in liposomes, microparticles, microcapsules, receptor-mediated endocytosis (Wu and Wu, *J. Biol. Chem.* 1987, 262:4429-32), and construction of therapeutic nucleic acids as part of a retroviral or other vector. Methods of introduction include, but are not limited to, intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal, vaginal and intestinal mucosa, etc.) and may be administered together with other biologically active agents. Administration can be systemic or local. Pharmaceutical compositions can be introduced into the central nervous system by any suitable route, including intraventricular and intrathecal injection; intraventricular injection may be facilitated by an intraventricular catheter, for example, attached to a reservoir, such as an Ommaya reservoir.

Liposomes fuse with the target site and deliver the contents of the lumen intracellularly. The liposomes are maintained in contact with the target cells for a sufficient time for fusion to occur, using various means to maintain contact, such as isolation and binding agents. Liposomes can be prepared with purified proteins or peptides that mediate fusion of membranes, such as Sendai virus or influenza virus. The lipids may be any useful combination of known liposome forming lipids, including cationic lipids, such as phosphatidylcholine. Other potential lipids include neutral lipids, such as cholesterol, phosphatidyl serine, phosphatidyl glycerol, and the like. For preparing the liposomes, the procedure described by Kato et al. (*J. Biol. Chem.* 1991, 266:3361) can be used.

Where the therapeutic molecule is a nucleic acid, administration can be achieved by an appropriate nucleic acid expression vector which is administered so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci. USA* 1991, 88:1864-8), etc. Alternatively, the nucleic acid can be introduced intracellularly and incorporated within host cell DNA for expression, by homologous recombination.

The vector pcDNA, is an example of a method of introducing the foreign cDNA into a cell under the control of a strong viral promoter (CMV) to drive the expression. However, other vectors can be used (see EXAMPLES 13 and 15). Other retroviral vectors (such as pRETRO-ON, Clontech), also use this promoter but have the advantages of entering cells without any transfection aid, integrating into the genome of target cells only when the target cell is dividing (as cancer cells do, especially during first remissions after chemotherapy) and they are regulated. It is also possible to turn on the expression of a nucleic acid by administering tetracycline when these plasmids are used.

Other plasmid vectors, such as pMAM-neo (Clontech) or pMSG (Pharmacia) use the MMTV-LTR promoter (which can be regulated with steroids) or the SV10 late promoter (pSVL, Pharmacia) or metallothionein-responsive promoter (pBPV, Pharmacia) and other viral vectors, including retroviruses. Examples of other viral vectors include adenovirus, AAV (adeno-associated virus), recombinant HSV, poxviruses (vaccinia) and recombinant lentivirus (such as HIV). These vectors achieve the basic goal of delivering into the target cell the cDNA sequence and control elements needed for transcription. The present disclosure includes all forms of nucleic acid delivery, including synthetic oligos, naked DNA, plasmid and viral, integrated into the genome or not.

Having illustrated and described methods for treating hemophilia A or B by oral administration of a therapeutically effective amount of F.VIII or F.IX, respectively, it should be apparent to one skilled in the art that the disclosure can be modified in arrangement and detail without departing from such principles. In view of the many possible embodiments to which the principles of our disclosure may be applied, it should be recognized that the illustrated embodiments are only particular examples of the disclosure and should not be taken as a limitation on the scope of the disclosure. Rather, the scope of the disclosure is in accord with the following claims. We therefore claim as our invention all that comes within the scope and spirit of these claims.

We claim:

1. A method for increasing hemostasis in a subject having hemophilia B in which clotting factor IX (F.IX) is deficient and wherein the subject does not have F.IX inhibitors, comprising orally administering to the subject a therapeutically effective amount of the F.IX sufficient to induce oral tolerance of the F.IX and supply exogenous F.IX to the subject, thereby increasing hemoslasis in the subject and treating the hemophilia B, wherein the F.IX is not present in a liposome.

2. The method of claim 1, wherein the hemophilia B is a result of impaired expression of the F.IX, and the F.IX is administered as long as the hemophilia B persists.

3. The method of claim 1, wherein increasing hemostasis comprises decreasing blood clotting time.

4. The method of claim 1, wherein the F.IX is administered in absence of an anti-immune therapy.

5. The method of claim 1, wherein the therapeutically effective amount of F.IX is at least 5 mg of F.IX per 1 kg of subject daily.

6. The method of claim 1, wherein the therapeutically effective amount of F.IX is at least 50 mg of F.IX per 1 kg of subject daily.

7. The method of claim 1, wherein the subject is a mammal.

8. The method of claim 7, wherein the mammal is a human.

9. The method of claim 1, wherein the F.IX is present in milk obtained from a non-human transgenic mammal expressing recombinant F.IX.

10. The method of claim 9, wherein the mammal is a pig.

11. The method of claim 3, wherein the blood clotting time is measured using an activated partial thromboplastin time (APTT) assay.

12. The method of claim 1, wherein oral administration is achieved by feeding the subject a therapeutically effective amount of the clotting factor.

13. The method of claim 12, wherein the F.IX is a recombinant F.IX present in milk of a non-human transgenic mammal.

14. The method of claim 1, wherein the F.IX is present in a pharmaceutically effective carrier.

15. The method of claim 14, wherein the pharmaceutically effective carrier is water.

16. The method of claim 14, wherein the pharmaceutically effective carrier is milk.

17. A method for increasing hemostasis and inducing oral tolerance in a subject having hemophilia B in which clotting factor IX (F.IX) is deficient and wherein the subject does not have F.IX inhibitors, consisting of orally administering to the subject the therapeutically effective amount of F.IX and at least one pharmaceutically acceptable carrier which is not a liposome.

18. A method for orally administering a recombinant clotting factor IX (F.IX) to a subject for treatment of hemophilia B in which F.IX is deficient, wherein the subject does not have inhibitors to F.IX, comprising orally administering a milk containing recombinant F.IX to the subject at a therapeutically effective amount such that hemostasis in the subject is increased and oral tolerance of F.IX is induced, thereby treating the hemophilia B.

19. The method of claim 18, wherein the milk comprises at least 2 g recombinant clotting factor IX per liter of milk.

20. The method of claim 19, wherein the milk is obtained from a non-human transgenic mammal.

21. The method of claim 20, wherein the mammal is a pig.

22. The method of claim 21, wherein the recombinant F.IX is present at a concentration of about 2 g per liter of the milk.

23. A method for orally administering a recombinant clotting factor IX (F.IX) to a subject for treatment of hemophilia B in which F.IX is deficient wherein the subject does not have inhibitors to F.IX, comprising:
expressing the recombinant F.IX in a non-human mammal such that the F.IX is expressed in milk of the mammal; and
orally administering the milk in which the F.IX has been expressed to the subject at a therapeutically effective amount such that blood cloning time in the subject is reduced and oral tolerance of the F.IX is induced, thereby treating the hemophilia B.

24. A method for orally administering a recombinant F.IX protein to a subject for treatment of hemophilia B, wherein the subject does not have inhibitors to F.IX, comprising orally administering milk containing recombinant F.IX protein to the subject at a therapeutically effective amount such that blood clotting time in the subject is reduced and oral tolerance of the recombinant F.IX protein is induced, thereby treating the hemophilia B.

25. A method of increasing hemostasis in a mammal having hemophilia B, comprising orally administering to the mammal 5-50 mg/kg/day of factor IX, wherein factor IX is not present in a liposome, and wherein the factor IX induces oral tolerance of the factor IX and supplies exogenous factor IX to the mammal, thereby increasing hemostasis in the mammal.

26. A method of increasing hemostasis in a mammal having hemophilia B, comprising orally administering to the mammal every other day 5-50 mg/kg of factor IX, wherein factor IX is not present in a liposome, and wherein the factor IX induces oral tolerance of the factor IX and supplies exogenous factor IX to the mammal, thereby increasing hemostasis in the mammal.

27. The method of claim 25, wherein the factor IX is recombinant factor IX present in milk of a non-human transgenic mammal.

28. The method of claim 26, wherein the factor IX is recombinant factor IX present in milk of a non-human transgenic mammal.

* * * * *

UNITED STATES PATENT AND TRADEMARK OFFICE
CERTIFICATE OF CORRECTION

PATENT NO. : 7,220,718 B2 Page 1 of 1
APPLICATION NO. : 10/485696
DATED : May 22, 2007
INVENTOR(S) : Alpan et al.

It is certified that error appears in the above-identified patent and that said Letters Patent is hereby corrected as shown below:

In the Specification:

Column 2, line 46, "product For" should be --product. For--.

Column 6, line 32, "Factor VIII (F.VIII) F.VIII" should be --Factor VIII (F.VIII): F.VIII--.

Column 26, line 44, "TILS" should be TILs--.

In the Claims:

Column 33, line 24, claim 1, "hemoslasis" should be --hemostasis--.

Column 34, line 31, claim 23, "cloning" should be --clotting--.

Signed and Sealed this

Twenty-fifth Day of December, 2007

JON W. DUDAS
*Director of the United States Patent and Trademark Office*